(12) United States Patent
Kawaoka et al.

(10) Patent No.: US 7,723,094 B2
(45) Date of Patent: May 25, 2010

(54) RECOMBINANT INFLUENZA VECTORS WITH A POLII PROMOTER AND RIBOZYMES FOR VACCINES AND GENE THERAPY

(75) Inventors: Yoshihiro Kawaoka, Middleton, WI (US); Stefan Hamm, River Vale, NJ (US); Hideki Ebihara, Winnipeg (CA)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/855,975

(22) Filed: May 27, 2004

(65) Prior Publication Data

US 2005/0037487 A1    Feb. 17, 2005

Related U.S. Application Data

(60) Provisional application No. 60/473,797, filed on May 28, 2003.

(51) Int. Cl.
C12N 7/02 (2006.01)
C12N 7/01 (2006.01)
C12N 15/09 (2006.01)
C12N 15/44 (2006.01)
C12N 15/86 (2006.01)

(52) U.S. Cl. .................. 435/239; 435/320.1; 435/235.1

(58) Field of Classification Search .................. 435/6, 435/5, 456, 69.1, 235.1; 514/44; 424/93.2
See application file for complete search history.

(56) References Cited

U.S. PATENT DOCUMENTS

| | | | | |
|---|---|---|---|---|
| 5,786,199 | A * | 7/1998 | Palese .................. | 435/239 |
| 6,270,958 | B1 * | 8/2001 | Olivo et al. .................. | 435/5 |
| 6,544,785 | B1 * | 4/2003 | Palese et al. .................. | 435/325 |
| 2002/0164770 | A1 * | 11/2002 | Hoffmann .................. | 435/235.1 |
| 2003/0035814 | A1 | 2/2003 | Kawaoka et al. | |
| 2004/0029251 | A1 * | 2/2004 | Hoffman et al. .................. | 435/239 |

FOREIGN PATENT DOCUMENTS

| EP | 1 201 760 | A1 * | 2/2002 |
| EP | 1201760 | A1 * | 2/2002 |
| WO | WO-2005/028658 | A2 | 3/2005 |

OTHER PUBLICATIONS

Taira et al., "Construction of a novel RNA-transcript-trimming plasmid which can be used both in vitro in place of run-off and(G)-free transcriptions and in vivo as multi-sequences transcription vectors," Nucleic Acids Research, vol. 19, No. 19, pp. 5125-5130 (1991).*
Taira et al. Nucleic Acids Research 19(19): 5125-5130, 1991.*
Feng et al. Archives of Virology 154:1151-1156, 2009. "The mouse Pol I terminator is more efficient than the hepatitis delta virus ribozyme in generating influenza-virus-like RNAs with precise 3' ends in a plasmid-only-based virus rescue system."*

"Avian Inluenza", Queensland Government—Department of Primary Industries, (Observed Feb. 22, 2003),2 pgs.
"Avian Inluenza", http://www.iah.bbsrc.ac.uk/reports/1997/ainf.html, (Observed Feb. 22, 2003), 2 pgs.
"International Search Report for corresponding PCT Application No. PCT/US2004/016649", (Apr. 18, 2005), 6 pgs.
"RNA World", http://faculty.uca.edu/~benw/biol4415/lecture10a/tsld003.htm, (Observed Feb. 25, 2003), 1 pg.
Blount, K. F., et al., "The Hammerhead Ribozyme", Biochemical Society Transactions, 30(6), (2002),1119-1122.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Cardona, C. J., "Avian Influenza", http://www.vetmed.ucdavis.edu/vetex/INF-PO_AvianInfluenzaFS.html, ((Observed Feb. 22, 2003), 3 pgs.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Du, Q., "Ribozyme Enzymology", http://academic.brooklyn.cuny.edu/chem/zhuang/QD/toppage1.htm, (Observed Feb. 25, 2003), 8 pgs.
Fodor, E., "Rescue of Influenza A Virus from Recombinant DNA", Journal of Virology, 73(11), (1999), 9679-9682.
Garrett, L., "Deadly Ebola, Avian Influenza Re-Emerging", Newsday.com, (Feb. 20, 2003),3 pgs.
Hoffmann, E. , et al., "Rescue of Influenza B Virus from Eigth Plasmids", Proc. Natl. Acad. USA, vol. 99 (17), (2002), 11411-11416.
Kijima, H. , et al., "Therapeutic Application of Ribozymes", Pharmac. Ther., 68(2), (1995), 247-267.
Kumar, P. K. R. et al., "Artificial Evolution and Natural Ribozymes", The FASEB Journal, 9, (1995),1183-1195.
Laxman, B., "Noninvasive Real-Time Imaging of Apoptosis", Proc. Natl. Acad. Sci. USA, 99(26), (2002),16551-16555.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998),542-547.
Neumann, G., "Generation of Influenza A Virus from Cloned cDNAs—historical Perspective and Outlook for the New Millenium", Reviews in Medical Virology, 12(1), (Jan. 2002),13-30.
Neumann, G. , "Generation of Influenza A Viruses Entirely from Cloned cDNAs", Proc. Natl. Acad. Sci. USA, 96, (1999),9345-9350.
Perdue, M. , et al., "Virulence and the Avian Influenza Virus Hemagglutinin Gene", United States Department of Agriculture—Agriculture Research Service, http://www.nps.ars.usda.gov/publications/publication.htm?SEQ_NO_155=106036,(Observed Feb. 22, 2003), 1 pg.

(Continued)

Primary Examiner—Mary E Mosher
(74) Attorney, Agent, or Firm—Schwegman, Lundberg & Woessner, P.A.

(57) ABSTRACT

The invention provides a composition useful to prepare influenza viruses, e.g., in the absence of helper virus, using vectors which include PolII promoters and multiple ribozyme sequences.

42 Claims, 17 Drawing Sheets

OTHER PUBLICATIONS

Pley, H. W., et al., "Three-Dimensional Structure of a Hammerhead Ribozyme", *Nature*, 372, (1994), 68-74.

Schnell, M. J., "Infectious Rabies Viruses From Cloned cDNA", *The EMBO Journal*, 13(18), (1994), 4195-4203.

"Australian Application Serial No. 2004274860, Office Action mailed May 21, 2008", 2 pgs.

"Chinese Application Serial No. 200480022014, First Office Action mailed Aug. 24, 2007", 6 pgs.

"European Application Serial No. 04809419.7, Communication mailed Apr. 3, 2007", 3 pgs.

"European Application Serial No. 04809419.7, Response filed Oct. 19, 2007 to Communication mailed Apr. 3, 2007", 20 pgs.

"Indian Application Serial No. 2388/KOLNP/2005, First Examination Report mailed Mar. 28, 2007", 10 pgs.

"International Application Serial No. PCT/US2004/016649, International Preliminary Report on Patentability mailed Dec. 15, 2005", 7 pgs.

"New Zealand Application Serial No. 543587, Examination Report mailed Mar. 1, 2007", 1 pg.

"New Zealand Application Serial No. 543587, Examination Report mailed Jul. 7, 2006", 2 pgs.

"New Zealand Application Serial No. 543587, Response filed Aug. 7, 2007 to Examination Reports mailed Jul. 7, 2006 and Mar. 1, 2007", 24 pgs.

"New Zealand Application Serial No. 543587, Second Examination Report mailed Feb. 25, 2008", 2 pgs.

"Singapore Application Serial No. 200507467-9, Invitation to Respond to Written Opinion mailed Jun. 19, 2007", 5 pgs.

\* cited by examiner

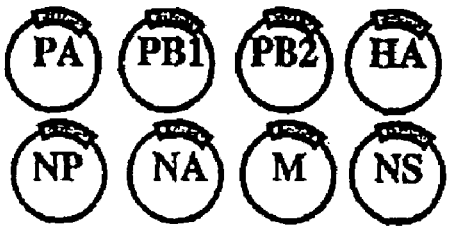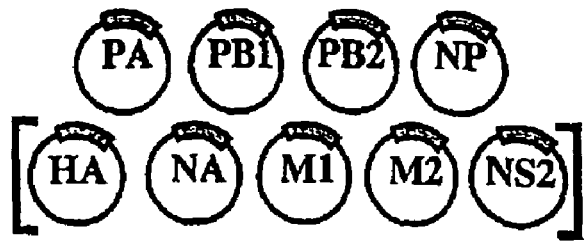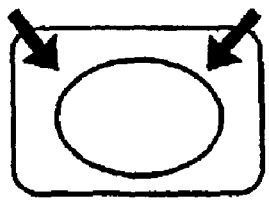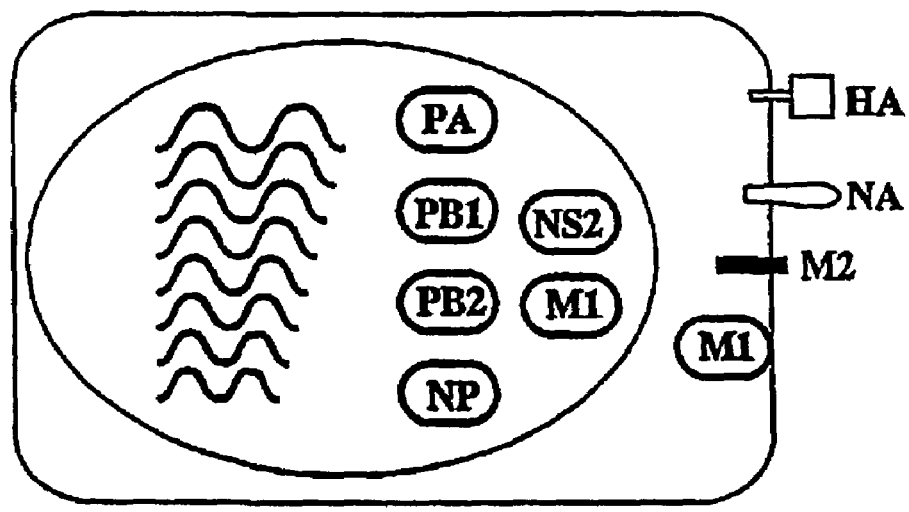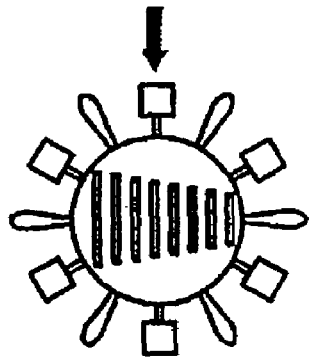
Fig. 3

PoII-5'WPB2
CAC ACA CGT CTC GTA TTA GTA GAA ACA AGG TCG TTT TTA AAC TAT TCG
ACA CTA ATT GAT GGC CAT CCG AAT TCT TTT GG
Length: 80 nt          Overlap: 26 nt

PoII-3'WPB2
CAC ACA CGT CTC CGG GAG CGA AAG CAG GTC AAT TAT ATT CAA TAT GGA
AAG AAT AAA AGA ACT AAG G
Length: 67 nt          Overlap: 24 nt

PoII-5'WPB1
CAC ACA CGT CTC GTA TTA GTA GAA ACA AGG CAT TTT TTC ATG AAG GAC
AAG CTA AAT TCA CTA TTT TTG CCG TCT GAG CTC TTC AAT GG
Length: 89          Overlap: 26 nt

PoII-3'WPB1
CAC ACA CGT CTC CGG GAG CGA AAG CAG GCA AAC CAT TTG AAT GGA TGT
CAA TCC GAC TTT ACT TTT C
Length: 67 nt          Overlap: 27 nt

PoII-5'WPA
CCA ACC CGT CTC CTA TTA GTA GAA ACA AGG TAC TTT TTT GGA CAG TAT
GGA TAG CAA ATA GTA GCA TTG CCA CAA CTA TCT CAA TGC ATG TGT GAG
GAA GGA G
Length:103          Overlap: 25 nt

PoII-3'WPA
CCA ACC CGT CTC CGG GAG CGA AAG CAG GTA CTG ATT CAA AAT GGA AGA
TTT TGT GCG ACA ATG CTT C
Length: 67 nt          Overlap: 27 nt

PoII-5'WHA
CAC ACA CGT CTC CTA TTA GTA GAA ACA AGG GTG TTT TTC C
Length: 40 nt          Overlap: 22 nt

PoII-3'WHA
CAC ACA CGT CTC CGG GAG CAA AAG CAG GGG AAA AT AAA AAC AAC C
Length: 46 nt          Overlap: 29 nt

Fig. 6A

PoII-5'WNP
CAC ACA *CGT CTC* CTA TTA GTA GAA ACA AGG GTA TTT TTC TTT AAT TG
Length: 47 nt                Overlap: 30 nt

PoII-3'WNP
CAC ACA *CGT CTC* CGG GAG CAA AAG CAG GGT AGA TAA TCA CTC
Length: 42 nt                Overlap: 26 nt

PoII-5'WNA
CAC ACA *CGT CTC* CTA TTA GTA GAA ACA AGG AGT TTT TTG AAC AAA C
Length: 46 nt                Overlap: 29 nt

PoII-3'WNA
CAC ACA *CGT CTC* CGG GAG CGA AAG CAG GAG TTT AAA TGA ATC CAA ACC
Length: 48 nt                Overlap: 32 nt

PoII-5'WM
CAC ACA *CGT CTC* CTA TTA GTA GAA ACA AGG TAG TTT TTT ACT CCA GC
Length: 47 nt                Overlap: 30 nt

PoII-3'WM
CAC ACA *CGT CTC* CGG GAG CAA AAG CAG GTA GAT ATT GAA AG
Length: 41 nt                Overlap: 26 nt

PoII-5'WNS
CAC ACA *CGT CTC* CTA TTA GTA GAA ACA AGG GTG TTT TTT ATT ATT AAA TAA GC
Length: 53 nt                Overlap: 36 nt

PoII-3'WNS
CAC ACA *CGT CTC* CGG GAG CAA AAG CAG GGT GAC AAA GAC ATA ATG G
Length: 46 nt                Overlap: 30 nt Italics:          BsmBI recognition sequence
Underlined:       Influenza virus sequence
Underlined + Bold: Influenza virus coding region

Fig. 6B

Fig 8

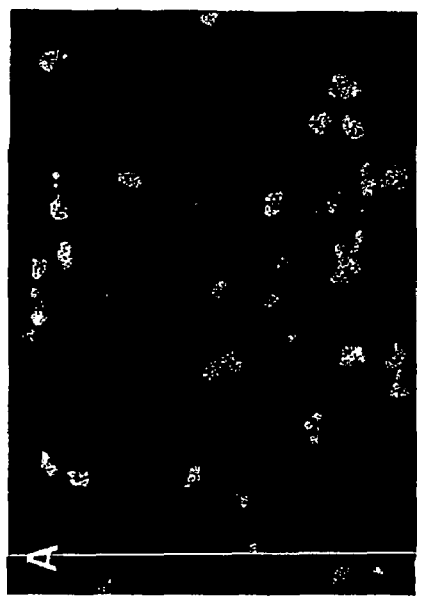
Fig 9

Replication of viral RNA and mRNA synthesis

Fig. 15

Pol I plasmids expressing vRNA of A/WSN/33

HA  NA  M  NS
PA  PB1  NP pCAGGS-2Ribo-PB2/483-627E

PB2 (E)

plasmids expressing viral proteins

PA  PB1  PB2  NP

WSN/HK3PB2-627E

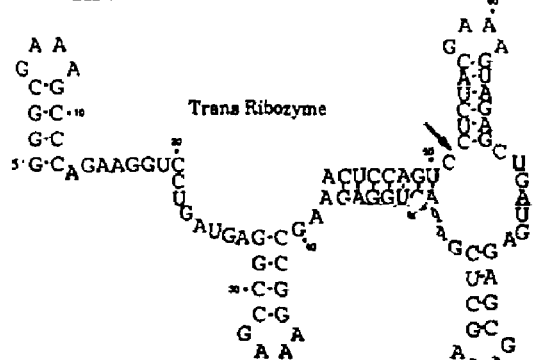
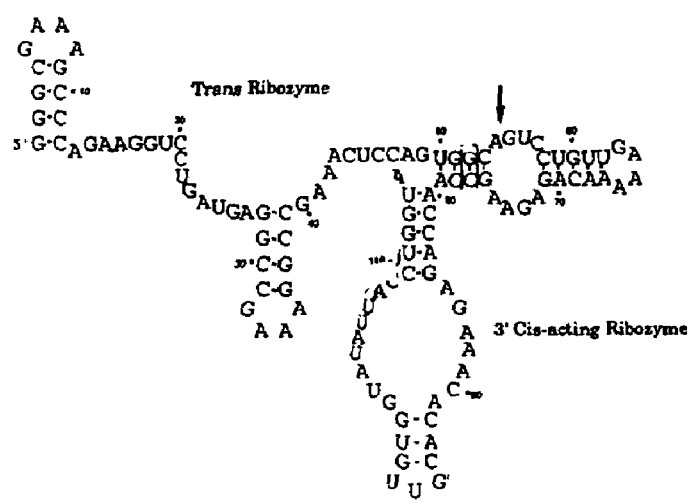
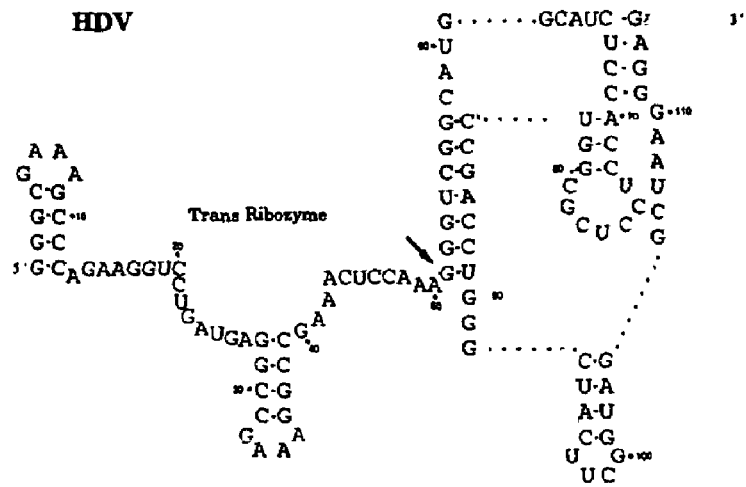
Fig 16

SEQUENCE LISTING

```
<160> NUMBER OF SEQ ID NOS: 37

<210> SEQ ID NO 1
<211> LENGTH: 80
<212> TYPE: DNA
<213> ORGANISM: Artificial Sequence
<220> FEATURE:
<223> OTHER INFORMATION: A synthetic primer

<400> SEQUENCE: 1
cacacacgtc tcgtattagt agaaacaagg tcgtttttaa actattcgac actaattgat      60
ggccatccga attcttttgg                                                  80

<210> SEQ ID NO 2
<211> LENGTH: 67
<212> TYPE: DNA
<213> ORGANISM: Artificial Sequence
<220> FEATURE:
<223> OTHER INFORMATION: A synthetic primer

<400> SEQUENCE: 2
```

-continued

```
cacacacgtc tccgggagcg aaagcaggtc aattatattc aatatggaaa gaataaaaga    60
actaagg                                                              67

<210> SEQ ID NO 3
<211> LENGTH: 89
<212> TYPE: DNA
<213> ORGANISM: Artificial Sequence
<220> FEATURE:
<223> OTHER INFORMATION: A synthetic primer

<400> SEQUENCE: 3
cacacacgtc tcgtattagt agaaacaagg cattttttca tgaaggacaa gctaaattca    60 ctattttgc cgtctgagct cttcaatgg                                       89

<210> SEQ ID NO 4
<211> LENGTH: 67
<212> TYPE: DNA
<213> ORGANISM: Artificial Sequence
<220> FEATURE:
<223> OTHER INFORMATION: A synthetic primer

<400> SEQUENCE: 4
cacacacgtc tccgggagcg aaagcaggca aaccatttga atggatgtca atccgacttt    60
acttttc                                                              67

<210> SEQ ID NO 5
<211> LENGTH: 103
<212> TYPE: DNA
<213> ORGANISM: Artificial Sequence
<220> FEATURE:
<223> OTHER INFORMATION: A synthetic primer

<400> SEQUENCE: 5
ccaacccgtc tcctattagt agaaacaagg tactttttg gacagtatgg atagcaaata    60
gtagcattgc cacaactatc tcaatgcatg tgtgaggaag gag                     103

<210> SEQ ID NO 6
<211> LENGTH: 67
<212> TYPE: DNA
<213> ORGANISM: Artificial Sequence
<220> FEATURE:
<223> OTHER INFORMATION: A synthetic primer

<400> SEQUENCE: 6
ccaacccgtc tccgggagcg aaagcaggta ctgattcaaa atggaagatt ttgtgcgaca    60
atgcttc                                                              67

<210> SEQ ID NO 7
<211> LENGTH: 40
<212> TYPE: DNA
<213> ORGANISM: Artificial Sequence
<220> FEATURE:
<223> OTHER INFORMATION: A synthetic primer

<400> SEQUENCE: 7
cacacacgtc tcctattagt agaaacaagg gtgttttcc                            40

<210> SEQ ID NO 8
<211> LENGTH: 45
<212> TYPE: DNA
<213> ORGANISM: Artificial Sequence
<220> FEATURE:
```

-continued

<223> OTHER INFORMATION: A synthetic primer

<400> SEQUENCE: 8
cacacacgtc tccgggagca aaagcagggg aaaataaaaa caacc         45

<210> SEQ ID NO 9
<211> LENGTH: 47
<212> TYPE: DNA
<213> ORGANISM: Artificial Sequence
<220> FEATURE:
<223> OTHER INFORMATION: A synthetic primer

<400> SEQUENCE: 9
cacacacgtc tcctattagt agaaacaagg gtattttct ttaattg         47

<210> SEQ ID NO 10
<211> LENGTH: 42
<212> TYPE: DNA
<213> ORGANISM: Artificial Sequence
<220> FEATURE:
<223> OTHER INFORMATION: A synthetic primer

<400> SEQUENCE: 10
cacacacgtc tccgggagca aaagcagggt agataatcac tc         42

<210> SEQ ID NO 11
<211> LENGTH: 46
<212> TYPE: DNA
<213> ORGANISM: Artificial Sequence
<220> FEATURE:
<223> OTHER INFORMATION: A synthetic primer

<400> SEQUENCE: 11
cacacacgtc tcctattagt agaaacaagg agtttttga acaaac         46

<210> SEQ ID NO 12
<211> LENGTH: 48
<212> TYPE: DNA
<213> ORGANISM: Artificial Sequence
<220> FEATURE:
<223> OTHER INFORMATION: A synthetic primer

<400> SEQUENCE: 12
cacacacgtc tccgggagcg aaagcaggag tttaaatgaa tccaaacc         48

<210> SEQ ID NO 13
<211> LENGTH: 47
<212> TYPE: DNA
<213> ORGANISM: Artificial Sequence
<220> FEATURE:
<223> OTHER INFORMATION: A synthetic primer

<400> SEQUENCE: 13
cacacacgtc tcctattagt agaaacaagg tagttttta ctccagc         47

<210> SEQ ID NO 14
<211> LENGTH: 41
<212> TYPE: DNA
<213> ORGANISM: Artificial Sequence
<220> FEATURE:
<223> OTHER INFORMATION: A synthetic primer

<400> SEQUENCE: 14
cacacacgtc tccgggagca aaagcaggta gatattgaaa g         41

<210> SEQ ID NO 15
<211> LENGTH: 53
<212> TYPE: DNA
<213> ORGANISM: Artificial Sequence
<220> FEATURE:
<223> OTHER INFORMATION: A synthetic primer

<400> SEQUENCE: 15
cacacacgtc tcctattagt agaaacaagg gtgtttttta ttattaaata agc         53

<210> SEQ ID NO 16
<211> LENGTH: 46
<212> TYPE: DNA
<213> ORGANISM: Artificial Sequence
<220> FEATURE:
<223> OTHER INFORMATION: A synthetic primer

<400> SEQUENCE: 16
cacacacgtc tccgggagca aaagcagggt gacaaagaca taatgg                 46

<210> SEQ ID NO 17
<211> LENGTH: 40
<212> TYPE: DNA
<213> ORGANISM: Artificial Sequence
<220> FEATURE:
<223> OTHER INFORMATION: A synthetic primer

<400> SEQUENCE: 17
gcatgcgaag acttgggtcg gcatggcatc tccacctcct                        40

<210> SEQ ID NO 18
<211> LENGTH: 31
<212> TYPE: DNA
<213> ORGANISM: Artificial Sequence
<220> FEATURE:
<223> OTHER INFORMATION: A synthetic primer

<400> SEQUENCE: 18
agatctaggg agctctccct tagccatccg a                                 31

<210> SEQ ID NO 19
<211> LENGTH: 64
<212> TYPE: DNA
<213> ORGANISM: Artificial Sequence
<220> FEATURE:
<223> OTHER INFORMATION: A synthetic oligolinker

<400> SEQUENCE: 19
aattctttct actctgatga gtccgtgagg acgaaaccCg gagtcccggg tcggagacga  60
tgca                                                               64

<210> SEQ ID NO 20
<211> LENGTH: 56
<212> TYPE: DNA
<213> ORGANISM: Artificial Sequence
<220> FEATURE:
<223> OTHER INFORMATION: A synthetic oligolinker

<400> SEQUENCE: 20
tcgtctccga cccgggactc cgggtttcgt cctcacggac tcatcagagt agaaag      56

<210> SEQ ID NO 21
<211> LENGTH: 24
<212> TYPE: DNA
<213> ORGANISM: Artificial Sequence
<220> FEATURE:

<223> OTHER INFORMATION: A synthetic primer

<400> SEQUENCE: 21
cgtctccggt cagtagaaac aagg                                              24

<210> SEQ ID NO 22
<211> LENGTH: 23
<212> TYPE: DNA
<213> ORGANISM: Artificial Sequence
<220> FEATURE:
<223> OTHER INFORMATION: A synthetic primer

<400> SEQUENCE: 22
cgtctccacc cagcaaaagc agg                                               23

<210> SEQ ID NO 23
<211> LENGTH: 96
<212> TYPE: RNA
<213> ORGANISM: Artificial Sequence
<220> FEATURE:
<223> OTHER INFORMATION: A synthetic hammerhead (HH) sequence

<400> SEQUENCE: 23
gggcgaaagc ccagaagguc cugaugaggc cgaaaggccg aagaggucaa agcucgaaag       60
cgagaguagu cgagaugaaa gcaucuccug accuca                                 96

<210> SEQ ID NO 24
<211> LENGTH: 115
<212> TYPE: RNA
<213> ORGANISM: Artificial Sequence
<220> FEATURE:
<223> OTHER INFORMATION: A synthetic hairpin (HP) sequence

<400> SEQUENCE: 24
gggcgaaagc ccagaagguc cugaugaggc cgaaaggccg aaacuccagu ggcaguccug       60
uugaaaaaca gagaagccaa ccagagaaac acacguugug guauauuacc uggua           115

<210> SEQ ID NO 25
<211> LENGTH: 110
<212> TYPE: RNA
<213> ORGANISM: Artificial Sequence
<220> FEATURE:
<223> OTHER INFORMATION: A synthetic HDV ribozyme sequence

<400> SEQUENCE: 25
gggcgaaagc ccagaagguc cugaugaggc cgaaaggccg aaacuccaaa gggucggcau       60
ggcaucucca ccuccucgcg guccgaccug ggcuacuucg guaggcuaag                 110

<210> SEQ ID NO 26
<211> LENGTH: 33
<212> TYPE: DNA
<213> ORGANISM: Artificial Sequence
<220> FEATURE:
<223> OTHER INFORMATION: A synthetic vector sequence

<400> SEQUENCE: 26
gggttattgg agacggtacc gtctcctccc ccc                                    33

<210> SEQ ID NO 27
<211> LENGTH: 33
<212> TYPE: DNA
<213> ORGANISM: Artificial Sequence
<220> FEATURE:
<223> OTHER INFORMATION: A synthetic vector sequence

```
<400> SEQUENCE: 27 gggggggagga gacggtaccg tctccaataa ccc                              33

<210> SEQ ID NO 28
<211> LENGTH: 18
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(18)
<223> OTHER INFORMATION: n = A,T,C or G

<400> SEQUENCE: 28
cgtctcntat tagtagaa                                                18

<210> SEQ ID NO 29
<211> LENGTH: 17
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(17)
<223> OTHER INFORMATION: n = A,T,C or G

<400> SEQUENCE: 29
ttttgctccc ngagacg                                                 17

<210> SEQ ID NO 30
<211> LENGTH: 17
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(17)
<223> OTHER INFORMATION: n = A,T,C or G

<400> SEQUENCE: 30
cgtctcnggg agcaaaa                                                 17

<210> SEQ ID NO 31
<211> LENGTH: 18
<212> TYPE: DNA
<213> ORGANISM: Artificial Sequence
<220> FEATURE:
<223> OTHER INFORMATION: A synthetic vector/influenza viral cDNA
      sequence
<220> FEATURE:
<221> NAME/KEY: misc_feature
<222> LOCATION: (1)...(18)
<223> OTHER INFORMATION: n = A,T,C or G

<400> SEQUENCE: 31
ttctactaat angagacg                                                18

<210> SEQ ID NO 32
<211> LENGTH: 11
<212> TYPE: DNA
<213> ORGANISM: Artificial Sequence
<220> FEATURE:
```

-continued

```
<223> OTHER INFORMATION: A synthetic vector/influenza viral cDNA
      sequence

<400> SEQUENCE: 32
tattagtaga a                                                         11

<210> SEQ ID NO 33
<211> LENGTH: 10
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 33
gggagcaaaa                                                           10

<210> SEQ ID NO 34
<211> LENGTH: 15
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 34
gggttattag tagaa                                                     15

<210> SEQ ID NO 35
<211> LENGTH: 13
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 35
ttttgctccc ccc                                                       13

<210> SEQ ID NO 36
<211> LENGTH: 13
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 36 gggggagca aaa                                                        13

<210> SEQ ID NO 37
<211> LENGTH: 15
<212> TYPE: DNA
<213> ORGANISM: Artificial Sequence
<220> FEATURE:
<223> OTHER INFORMATION: A synthetic vector/influenza viral cDNA
      sequence

<400> SEQUENCE: 37
ttctactaat aaccc                                                     15
```

RECOMBINANT INFLUENZA VECTORS WITH A POLII PROMOTER AND RIBOZYMES FOR VACCINES AND GENE THERAPY

CROSS-REFERENCE TO RELATED APPLICATIONS

The present application claims the benefit under 35 U.S.C. §119(e) of the filing date of U.S. Application Ser. No. 60/473,797, filed May 28, 2003, the disclosure of which is incorporated by reference herein.

STATEMENT OF GOVERNMENT RIGHTS

This invention was made with a grant from the Government of the United States of America (grant AI-47446 from the National Institute of Allergy and Infectious Diseases Public Health Service). The Government may have certain rights in the invention.

BACKGROUND OF THE INVENTION

Negative-sense RNA viruses are classified into seven families (Rhabdoviridae, Paramyxoviridae, Filoviridae, Bornaviridae, Orthomyxoviridae, Bunyaviridae, and Arenaviridae) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

In order to initiate viral replication of negative-stranded RNA viruses, vRNA(s) or cRNA(s) must be coexpressed with the polymerase complex and the nucleoprotein. Rabies virus was the first non-segmented negative-sense RNA virus which was generated entirely from cloned cDNA: Schnell et al. (1994) generated recombinant rabies virus by cotransfection of a cDNA construct encoding the full-length cRNA and protein expression constructs for the L, P, and N proteins, all under control of the T7 RNA polymerase promoter. Infection with recombinant vaccinia virus, which provided T7 RNA polymerase, resulted in the generation of infectious rabies virus. In this T7 polymerase system, the primary transcription of the full length cRNA under control of the T7 RNA polymerase resulted in a non-capped cRNA transcript. However, three guanidine nucleotides, which form the optimal initiation sequence for T7 RNA polymerase, were attached to the 5' end. In order to create an authentic 3' end of the cRNA transcript which is essential for a productive infective cycle, the hepatitis delta ribozyme (HDVRz) sequence was used for exact autocatalytic cleavage at the 3' end of the cRNA transcript.

Since the initial report by Schnell et al. (1994), reverse genetics systems using similar techniques led to the generation of many non-segmented negative strand RNA viruses (Conzelmann, 1996; Conzelmann, 1998; Conzelmann et al., 1996; Marriott et al., 1999; Munoz et al., 2000; Nagai, 1999; Neumann et al., 2002; Roberts et al., 1998; Rose, 1996). Refinements of the original rescue procedure included the expression of T7 RNA polymerase from stably transfected cell lines (Radecke et al., 1996) or from protein expression plasmids (Lawson et al., 1995), or heat shock procedures to increase rescue efficiencies (Parks et al., 1999). Based on the T7 polymerase system, Bridgen and Elliott (1996) created Bunyamwera virus (family Bunyaviridae) from cloned cDNAs and demonstrated the feasibility of artificially generating a segmented negative-sense RNA virus by the T7 polymerase system.

In 1999, a plasmid-based reverse genetics technique was generated based on the cellular RNA polymerase I for the generation of segmented influenza A virus entirely from cloned cDNAs (Fodor et al., 1999; Neumann and Kawaoka, 1999). RNA polymerase I, a nucleolar enzyme, synthesizes ribosomal RNA which, like influenza virus RNA, does not contain 5' cap or 3' polyA structures. The RNA polymerase I transcription of a construct containing an influenza viral cDNA, flanked by RNA polymerase I promoter and terminator sequences, resulted in influenza vRNA synthesis (Fodor et al., 1999; Neumann and Kawaoka, 1999; Neumann and Kawaoka, 2001; Pekosz et al., 1999). The system was highly efficient, producing more than $10^8$ infectious virus particles per ml of supernatant of plasmid-transfected cells 48 hours post-transfection. However, the host cell specificity of RNA polymerase I restricts the use of the RNA polymerase I system. For instance, the promoter sequence of the human RNA polymerase I promoter is not recognized by a heterologous RNA polymerase I, e.g., murine RNA polymerase I (Grummt et al., 1982; Learned et al., 1982).

Thus, what is needed is an improved method to prepare segmented, negative strand RNA viruses, e.g., orthomyxoviruses such as influenza A virus, entirely from cloned cDNAs.

SUMMARY OF THE INVENTION

The invention provides at least one of the following isolated and/or purified vectors: a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, a vector comprising a promoter operably linked to an influenza virus NS cDNA linked to a transcription termination sequence, a vector comprising a promoter operably linked to an influenza virus NA and NB cDNA linked to a transcription termination sequence, or a vector comprising a promoter operably linked to an influenza virus BM2 cDNA linked to a transcription termination sequence, wherein the vector comprises a RNA polymerase II promoter linked to a first (5') ribozyme sequence linked to the viral cDNA which is linked to a second (3') ribozyme sequence linked to a transcription termination sequence. Ribozymes within the scope of the invention include, but are not limited to, tetrahymena ribozymes, RNase P, hammerhead ribozymes, hairpin ribozymes, hepatitis ribozyme, as well as synthetic ribozymes (for exemplary ribozymes see Kumar et al. (1995); Pley et al. (1994); Chowrira et al. (1994); Kijima et al. (1995); and U.S. Pat. Nos. 5,631,115 and 5,683, 902). The ribozyme sequences in a vector comprising the RNA polymerase II promoter may be the same or different, and, when a plurality of vectors comprising a RNA polymerase II promoter are employed, each vector may comprise the same or different ribozyme sequences relative to any other vector. Similarly, the RNA polymerase II promoter in one vector may be the same or different than the RNA polymerase II promoter in a different vector. The cDNA may be in the sense or antisense orientation relative to the promoter. Thus, a vector of the invention may encode an orthomyxovirus protein (sense) or vRNA (antisense). Any suitable promoter or transcription termination sequence may be employed to express a protein, e.g., a viral protein, a protein of a nonviral pathogen, or a therapeutic protein.

In one embodiment, one or more vectors for vRNA production comprise a RNA polymerase II promoter. In another embodiment, one or more, but not all, vectors for vRNA production comprise a promoter other than a RNA polymerase II promoter, promoters including, but not limited to, a RNA polymerase I promoter, e.g., a human RNA polymerase I promoter, a RNA polymerase III promoter, a T7 promoter, or a T3 promoter. If present, the transcription termination sequence in the vector for vRNA comprising the RNA polyermase II promoter is preferably a RNA polymerase II transcription termination sequence, which is 3' to the 3' ribozyme sequence. Preferred transcription termination sequences for the vRNA vectors that do not comprise a RNA polymerase II promoter include, but are not limited to, a RNA polymerase I transcription termination sequence, a RNA polymerase III transcription termination sequence, or a ribozyme. Preferably, the vectors comprise influenza cDNA, e.g., influenza A (e.g., any influenza A gene including any of the 15 HA or 9 NA subtypes), B or C DNA (see Chapters 45 and 46 of Fields Virology (Fields et al. (eds.), Lippincott-Raven Publ., Philadelphia, Pa. (1996), which are specifically incorporated by reference herein), although it is envisioned that the gene(s) of any virus may be employed in the vectors or methods of the invention.

The invention provides a composition comprising a plurality of the orthomyxovirus vectors of the invention. In one embodiment of the invention, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence, wherein at least one vector comprises a RNA polymerase II promoter 5' to a first ribozyme sequence, which is 5' to a sequence corresponding to viral coding sequences, which is 5' to a second ribozyme sequence, which is 5' to a transcription termination sequence; and b) at least two vectors selected from a vector encoding influenza virus PA, a vector encoding influenza virus PB1, a vector encoding influenza virus PB2, and a vector encoding influenza virus NP. Optionally, the vectors of b) include one or more vectors encoding NP, NS, M, e.g., M1 and M2, HA or NA.

In another embodiment, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA and NB cDNA linked to a transcription termination sequence, a vector comprising a promoter operably linked to an influenza virus M cDNA linked to a transcription termination sequence, a vector comprising a operably linked to an influenza virus NS cDNA linked to a transcription termination sequence, and a vector comprising a promoter operably linked to an influenza virus BM2 cDNA linked to a transcription termination sequence, wherein at least one vector comprises a RNA polymerase II promoter 5' to a first ribozyme sequence, which is 5' to a sequence corresponding to viral sequences including viral coding sequences, which is 5' to a second ribozyme sequence, which is 5' to a transcription termination sequence; and b) at least two vectors selected from a vector encoding influenza virus PA, a vector encoding influenza virus PB1, a vector encoding influenza virus PB2, and a vector encoding influenza virus NP. Optionally, the vectors of b) include one or more vectors encoding NP, NS, M, HA or NA.

Preferably, the vectors encoding viral proteins further comprise a transcription termination sequence. It is preferred that a promoter for the vectors comprising influenza virus cDNA include a RNA polymerase I promoter, a RNA polymerase II promoter, a RNA polymerase III promoter, a T7 promoter, and a T3 promoter, however, at least one vector for vRNA comprises a RNA polymerase II promoter. The vector for vRNA comprising the RNA polymerase II promoter comprises viral coding sequences flanked by ribozyme sequences, and optionally a RNA polymerase II transcription termination sequence which is 3' to the 3' ribozyme sequence. In one embodiment, one or more, but not all of the vectors for vRNA production include a transcription termination sequence, e.g., a RNA polymerase I transcription termination sequence, a RNA polymerase II transcription termination sequence, a RNA polymerase III transcription termination sequence, or a ribozyme. In one embodiment, at least 2 and preferably more, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same. Preferably, the vectors comprise influenza DNA, e.g., influenza A, B or C DNA.

Another embodiment of the invention comprises a composition of the invention as described above further comprising a vector comprising a promoter linked to 5' orthomyxovirus sequences optionally including 5' orthomyxovirus coding sequences or a portion thereof, linked to a desired nucleic acid sequence, e.g., a desired cDNA, linked to 3' orthomyxovirus sequences optionally including 3' orthomyxovirus coding sequences or a portion thereof, linked to a transcription termination sequence. Preferably, the desired nucleic acid sequence such as a cDNA is in an antisense orientation. The introduction of such a composition to a host cell permissive for orthomyxovirus replication results in recombinant virus comprising vRNA corresponding to sequences of the vector comprising 5' orthomyxovirus sequences optionally including 5' orthomyxovirus coding sequences or a portion thereof linked to the cDNA linked to 3' orthomyxovirus sequences optionally including 3' orthomyxovirus coding sequences or a portion thereof. The promoter in such a vector for vRNA production may be a RNA polymerase I promoter, a RNA polymerase II promoter, a RNA polymerase III promoter, a T7 promoter, and a T3 promoter, and optionally the vector comprises a transcription termination sequence such as a RNA polymerase I transcription termination sequence, or a RNA polymerase II transcription termination sequence, a RNA polymerase III transcription termination sequence, or a ribozyme. In one embodiment, the vector comprising the desired cDNA (cDNA of interest) comprises a RNA polymerase II promoter linked to a first ribozyme sequence linked to the cDNA of interest linked to a second ribozyme sequence linked to a transcription termination sequence. In another embodiment, the vector comprises a RNA polymerase II promoter linked to a first ribozyme sequence linked to 5' orthomyxovirus sequences optionally including 5' orthomxyovirus coding sequences or a portion thereof linked to the cDNA of interest linked to 3' orthomyxovirus sequences optionally including 3' orthomxyovirus coding sequences or a portion thereof linked to a second ribozyme sequence linked to a transcription termination sequence. In another embodiment, the cDNA of interest may be present in a vector for protein expression. The cDNA of interest, whether in a vector for vRNA or protein production may encode an immunogenic epitope, such as an epitope useful in a cancer therapy or vaccine, or gene therapy.

A plurality of the vectors of the invention may be physically linked or each vector may be present on an individual plasmid or other, e.g., linear, nucleic acid delivery vehicle.

The invention also provides a method to prepare influenza virus. The method comprises contacting a cell with a plurality of the vectors of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or virus of the invention. In another embodiment, the invention includes contacting the cell with one or more vectors, either vRNA or protein production vectors, prior to other vectors, either vRNA or protein production vectors.

As described hereinbelow, influenza A viruses were prepared entirely from cloned cDNAs. Moreover, the same approach may be employed for other viruses to generate nonsegmented negative strand RNA viruses (i.e., Paramyxoviridae, Rhabdoviridae, and Filoviridae), or other segmented negative strand RNA viruses, e.g., Arenaviridae and Bunyaviridae, entirely from cloned cDNA.

The method of the invention allows easy manipulation of influenza viruses, e.g., by the introduction of attenuating mutations into the viral genome. Further, because influenza viruses induce strong humoral and cellular immunity, the invention greatly enhances these viruses as vaccine vectors, particularly in view of the availability of natural variants of the virus, which may be employed sequentially, allowing repetitive use for gene therapy.

Thus, the invention provides isolated and purified vectors or plasmids, which express or encode influenza virus proteins, or express or encode influenza vRNA, both native and recombinant vRNA. Thus, a vector or plasmid of the invention may comprise a gene or open reading frame of interest, e.g., a foreign gene encoding an immunogenic peptide or protein useful as a vaccine. Preferably, the vector or plasmid which expresses influenza vRNA comprises a promoter suitable for expression in a particular host cell, e.g., avian or mammalian host cells such as canine, feline, equine, bovine, ovine, or primate cells including human cells, or preferably, for expression in more than one host. Also preferably, one or more vectors or plasmids comprising DNA useful to prepare influenza vRNA comprise RNA polymerase II transcription termination sequences. For vectors or plasmids comprising a gene or open reading frame of interest, it is preferred that the gene or open reading frame is flanked by 5' and 3' influenza virus sequences including 5' and $_3$' non-coding sequences, respectively, of influenza virus, and in one embodiment, that the gene or open reading frame flanked by 5' and 3' influenza virus sequences is operably linked to a RNA polymerase II promoter and a RNA polymerase II transcription termination sequence. When preparing virus, the vector or plasmid comprising the gene or open reading frame may substitute for a vector or plasmid for an influenza viral gene or may be in addition to vectors or plasmids for all influenza viral genes.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) is provided.

The invention also provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor-specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. Preferably, the mammal is a human.

BRIEF DESCRIPTION OF THE DRAWINGS

FIG. 3. Proposed reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.

FIGS. 6A and 6B. Primers employed to amplify influenza sequences (SEQ ID NOS:1-16).

FIG. 8. The PA, PB1, PB2, and NP proteins of influenza A virus encapsidate GFP vRNA produced by RNA polymerase I, leading to GFP expression. 293T cells were transfected with plasmids expressing the PB2, PB1, PA and NP proteins (A) or with all plasmids except the one expressing the NP protein (B), together with the RNA polymerase I-GFP gene plasmid for intracellular synthesis of reporter gene vRNA. Cells were fixed 48 hours after transfection, and GFP expression was determined with a fluorescence microscope.

FIG. 9. Generation of infectious influenza VLPs. 293T cells were transfected with nine plasmids, each expressing a different viral structural protein (A), or with eight plasmids omitting the construct for NP (B), together with the RNA polymerase I-GFP gene plasmid. Forty-eight hours after transfection, VLP-containing supernatants were collected, mixed with A/WSN/33 helper virus, and inoculated into MDCK cells. Cells were fixed at 10 hours after infection, and GFP expression was determined with a fluorescence microscope.

FIG. 15. Generation of WSN/HK3PB2-627E virus from cloned cDNAs. PA, PB1, NP, M, NS, NA, and HA vRNAs of A/WSN/33 are synthesized by an RNA polymerase I system, whereas PB2 vRNA of WSN/HK3PB2-627E is provided by the RNA polymerase II/double ribozyme system. The viral NP and polymerase proteins, expressed by protein expression constructs, replicate and transcribe the vRNAs, resulting in the synthesis of all viral proteins and the generation of replicating influenza virus.

FIG. 16. Exemplary hammerhead (HH), hairpin (HP) and HDV ribozyme sequences (SEQ ID NOS:23-25). Solid arrows indicate self-processing sites.

DETAILED DESCRIPTION OF THE INVENTION

Definitions

Figure 1:
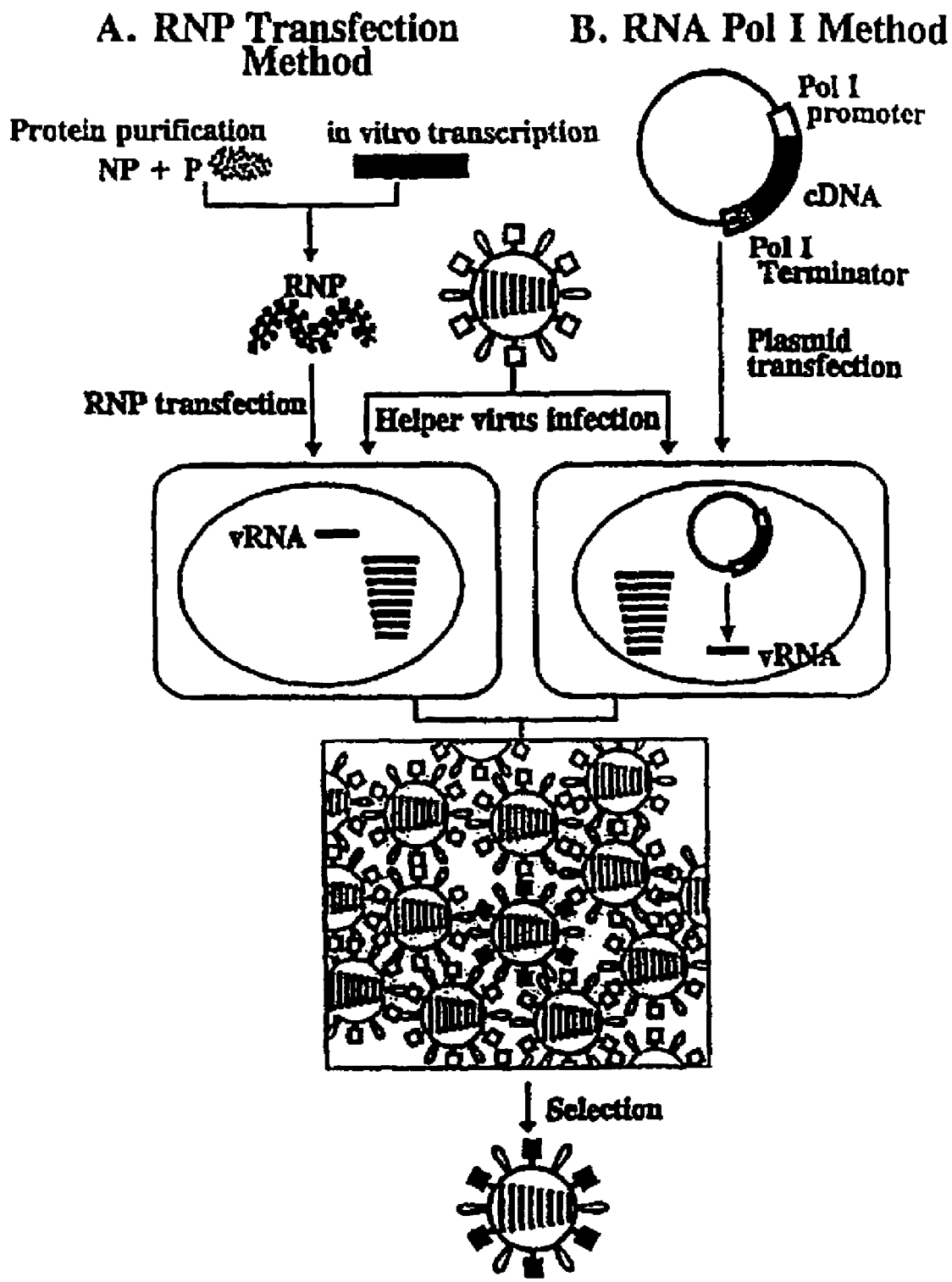
FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuramimidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity. Similarly, influenza C virus does not have a M2 protein with ion channel activity. However, the CM1 protein is likely to have this activity. The activity of an ion channel protein may be measured by methods well-known to the art, see, e.g., Holsinger et al. (1994) and WO 01/79273.

Thogotovirus

Thogotoviruses (THOV) represent a new genus in the family of Orthomyxoviridae. They are transmitted by ticks and have been found in domestic animals, including camels, goats, and cattle. Consequently, THOV can replicate in tick and vertebrate cells. The THOV genome comprises six segments of single-stranded, negative-sense RNA. The proteins encoded by the three largest segments show significant homology to the influenza virus polymerase proteins PB2, PB1, and PA. Segment 5 encodes a protein related to influenza virus NP. The THOV glycoprotein, which is encoded by segment 4, is not homologous to either influenza virus HA or NA, but it shows sequence similarity to the Baculovirus glycoprotein. The smallest segment is thought to encode a matrix protein and does not resemble any of the influenza virus proteins. Like influenza virus, both the 3' and 5' ends of the vRNA are required for promoter activity, and this activity is located in the terminal 14 and 15 nucleotides of the 3' and 5' ends of the vRNA, respectively.

The mRNA synthesis of THOV is primed by host cell-derived cap structures. However, in contrast to influenza virus, only the cap structures (without additional nucleotides) are cleaved from cellular mRNAs (Albo et al., 1996; Leahy et al., 1997; Weber et al., 1996). In vitro cleavage assays revealed that both the 5' and 3' ends of vRNA are required for endonuclease activity (Leahy et al., 1998), but addition of a model cRNA promoter does not stimulate endonuclease activity (Leahy et al., 1998), as has been shown for influenza virus (Cianci et al., 1995; Hagen et al., 1994). A 'hook' structure has been proposed for THOV (Leahy et al., 1997; Weber et al., 1997), which is similar to the corkscrew structure proposed for influenza virus (Flick et al., 1996). This 'hook' structure, however, is only found in the THOV vRNA promoter. The cRNA promoter sequence does not allow the formation of base pairs between positions 2 and 9, and between 3 and 8 at the 5' end of the cRNA. Alterations at positions 3 or 8 to allow base-pairing between these nucleotides stimulates endonuclease activity, which is strong supporting evidence of the proposed 'hook' structure (Leahy et al., 1998). Moreover, this structure might be crucial for the regulation of the THOV life cycle; the vRNA promoter, forming the 'hook' structure, may stimulate PB2 endonuclease activity, thereby allowing transcription. The cRNA promoter, in contrast, may not form the 'hook' structure and may therefore be unable to stimulate endonuclease activity, thus resulting in replication.

Bunyaviridae

The family Bunyaviridae includes several viruses that cause hemorrhagic or encephalitic fevers in humans (e.g., Rift fever valley, Hantaan, La Crosse, and Crimean-Congo hemorrhagic fever). The spherical and enveloped virions contain three segments of single-stranded, negative-sense RNA (reviewed in Elliott, 1997). The largest segment (L) encodes the viral RNA polymerase protein (L protein), whereas the M segment encodes the two viral glycoproteins G1 and G2, and a nonstructural protein (NSm). The smallest segment (S) encodes the nucleocapsid protein (N) and a second nonstructural protein (NSs). Virus replication and transcription take place in the cytoplasm, and newly assembled virions bud through the membranes of the Golgi apparatus.

Bridgen & Elliott (1996) have established a reverse genetics system to generate infectious Bunyamwera virus entirely from cloned cDNAs. They followed a strategy first described by Schnell et al. (1994) for rabies virus: intracellular transcription of a cDNA coding for the positive-sense antigenomic RNA (but not for the negative-sense genomic RNA) in cells expressing the viral polymerase and nucleoprotein. Bridgen & Elliott (1996) infected HeLaT4+ cells with vaccinia virus expressing T7 polymerase and transfected these cells with plasmids expressing proteins encoded by the S, M, and L segments. They then transfected these cells with three plasmids encoding full-length anti-genomic cDNAs flanked by the T7 polymerase promoter and the hepatitis delta virus ribozyme. To increase the number of bunyavirus particles relative to the number of vaccinia virus particles, the authors used mosquito cells in which Bunyamwera but not Vaccinia virus replicates. This protocol can be used not only to genetically engineer Bunyaviridae, but also generate reassortant viruses that cannot easily be obtained by coinfecting cells with different Bunyaviridae strains.

To study bunyavirus promoter elements and the viral proteins that are required for transcription and replication, Dunn et al. (1995) cloned the CAT gene in the negative-sense orientation between the 5' and 3' nontranslated regions of the Bunyamwera S RNA segment. Cells were transfected with constructs expressing the proteins encoded by the L and S segment and were then transfected with in vitro transcribed RNA, which resulted in CAT activity. The bunyavirus S segment encodes two proteins, N and NSs, in overlapping reading frames. To determine whether both of these proteins are required for transcription and replication, constructs expressing only N or NSs were tested for CAT activity. N protein expression, together with L protein, resulted in CAT activity, whereas no CAT activity was detected with the NSs expression construct. Thus, the L and N proteins are sufficient for transcription and replication of a bunyavirus-like RNA.

As with influenza virus, the terminal sequences of bunyavirus RNAs are complementary and highly conserved. It has therefore been assumed that these sequence elements define the bunyaviral promoter and are crucial for promoter activity. Deletion of five nucleotides at the 3' end of the viral RNA drastically reduces CAT expression (Dunn et al., 1995). In contrast, addition of two nucleotides at the 5' end, or of 11 or 35 nucleotides at the 3' end does not abolish CAT expression (Dunn et al., 1995). Therefore, like the influenza virus polymerase complex, the bunyavirus polymerase protein can apparently start transcription and/or replication internally.

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centriftigation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Layer & Webster, 1976; Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuramimidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reasserted virus according to known methods (see, e.g., Murphy, 1993). Since resistance to influenza A virus is mediated by the development of an immune response to the HA and NA glycoproteins, the genes coding for these surface antigens must come from the reassorted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants H1N1 and H3N2 vaccine candidates in a manner analogous to that described above for the A/AA/6/60 ca donor virus. Similarly, other known and suitable attenuated donor strains can be reasserted with influenza virus of the invention to obtain attenuated vaccines suitable for use in the vaccination of mammals (Ewami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Goodman et al., 1990; *Avery's Drug Treatment,* 1987; Osol, 1980; Katzung, 1992. The composition of the invention is generally presented in the form of individual doses (unit doses).

Conventional vaccines generally contain about 0.1 to 200 µg, preferably 10 to 15 µg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Goodman et al., 1990; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; Goodman et al., 1990; Avery, 1987; and Katzung, 1992. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Goodman et al., 1990; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Goodman et al., 1990; Avery's, 1987; Ebadi, 1985; and Katzung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children 3 years of age, and 7.5 µg per component for older children <3 years of age. The quantity of NA can also be standardized, however, this glycoprotein can be labile during the processor purification and storage (Kendal et al., 1980; Kerr et al., 1975). Each 0.5-ml dose of vaccine preferably contains approximately 1-50 billion virus particles, and preferably 10 billion particles.

The invention will be further described by the following examples.

EXAMPLE 1

Materials and Methods

Cells and viruses. 293T human embryonic kidney cells and Madin-Darby canine kidney cells (MDCK) were maintained in Dulbecco's modified Eagle medium (DMEM) supplemented with 10% fetal calf serum and in modified Eagle's medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10-day-old eggs.

Figure 2:
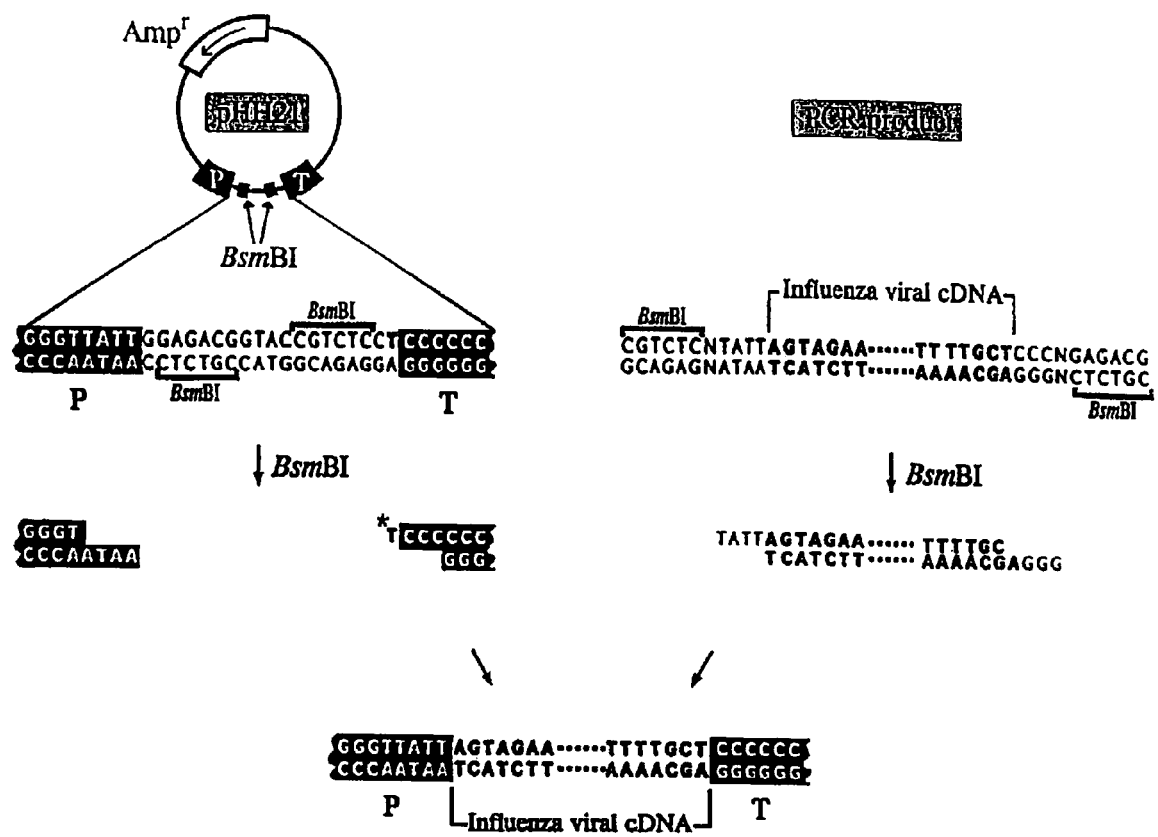
FIG. 2. Schematic diagram of the generation of RNA polymerase I constructs. cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA. Influenza A virus sequences are shown in bold face letters. (SEQ ID NOs:26-37)

Construction of plasmids. To generate RNA polymerase I constructs, cloned cDNAs derived from A/WSN/33 or A/PR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS1, respectively. The PB1 gene of influenza A/PR/8/34 virus was amplified by using pcDNA774 (PB1) (Perez et al., 1998) as a template. See FIG. 6 for the sequences of the primers. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of A/WSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN-NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774(PB1), pcDNA762(PB2), and pcDNA787(PA) were used to express the PB2, PB1, and PA proteins under control of the cytomegalovirus promoter (Perez et al., 1998).

Generation of infectious influenza particles. 293T cells ($1 \times 10^6$) were transfected with a maximum of 17 plasmids in different amounts with use of Trans IT LT-1 (Panvera, Madison, Wis.) according to the manufacturer's instructions. Briefly, DNA and transfection reagent were mixed (2 µl Trans IT-LT-1 per µg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the percentage of plasmid-transfected cells producing viruses. Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining assay. Nine hours after infection with influenza virus, cells were washed twice with phosphate-buffered saline (PBS) and fixed with 3.7% paraformaldehyde (in PBS) for 20 minutes at room temperature. Next, they were treated with 0.1% Triton X-100 and processed as described by Neumann et al. (1997).

Results

Generation of infectious virus by plasmid-driven expression of viral RNA segments, three polymerase subunits and NP protein. Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). $1 \times 10^6$ 293T cells were transfected with protein expression plasmids (1 µg of pcDNA762(PB2), 1 µg of pcDNA774(PB1), 0.1 µg of pcDNA787(PA), and 1 µg of pCAGGS-WSN-NP0/14) and 1 µg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after transfection of 293T cells, $7 \times 10^3$ pfu of virus per ml was found in the supernatant (Experiment 1, Table 1), demonstrating for the first time the capacity of reverse genetics to produce influenza A virus entirely from plasmids.

availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 µg of pcDNA762 (PB2) and pcDNA774(PB1); 0.1 µg of pcDNA787(PA); 1 µg of pEWSN-HA, pCAGGS-WSN-NP0/14, and pCAGGS-WNA15; 2 µg of pCAGGS-WSN-M1-2/1; 0.3 µg of pCA-NS2; and 0.03 µg of pEP24c (for M2), together with 1 µg of each RNA polymerase I plasmid (Experiment 2, Table 1). A second set of cells was transfected with the same set of RNA polymerase I plasmids, with the exception of the PB1 gene, for which pPolI-PR/8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5-8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, >$10^3$ pfu/ml, had increased to >$10^6$ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in 103.3 cells was generating infectious virus particles.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:† | | | | | | | | |
| PB1 | + | + | − | − | − | − | − | − |
| PR8-PB1 | − | − | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |
| M | + | + | + | + | + | + | + | + |
| NS | + | + | + | + | + | + | + | + |
| Protein expression plasmids for: | | | | | | | | |
| PB1 | + | + | + | + | + | | + | + |
| PB2 | + | + | + | + | + | + | − | + |
| PA | + | + | + | + | + | + | − | + |
| NP | + | + | + | + | + | + | + | − |
| HA | − | + | − | + | + | + | + | + |
| NA | − | + | − | + | + | + | + | + |
| M1 | − | + | − | + | + | + | + | + |
| M2 | − | + | − | + | + | + | + | + |
| NS2 | − | + | − | + | + | + | + | + |
| Virus titer (pfu/ml) | $7 \times 10^3$ | $7 \times 10^3$ | $1 \times 10^3$ | $3 \times 10^4$ | 0 | 0 | 0 | 0 |

*293T cells were transfected with the indicated plasmids. Twenty-four (Experiments 1 and 2) or forty-eight hours (Experiments 3-8) later, the virus titer in the supernatant was determined in MDCK cells.
†Unless otherwise indicated, plasmids were constructed with cDNAs representing the RNAs of A/WSN/33 virus.

Efficiency of influenza virus production with coexpression of all viral structural proteins. Although expression of the viral NP and polymerase proteins is sufficient for the plasmid-driven generation of influenza viruses, it was possible that the efficiency could be improved. In previous studies, the expression of all influenza virus structural proteins (PB2, PB1, PA, HA, NP, NA, M1, M2, and NS2) resulted in VLPs that contained an artificial vRNA encoding a reporter chloramphenicol-acetyltransferase gene (Mena et al., 1996). Thus, the

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 2 |
| 6 | 0 | ND | ND |
| 12 | 0 | ND | 0 |
| 18 | 0 | ND | 0 |
| 24 | 0 | $2 \times 10^3$ | $6 \times 10^3$ |
| 30 | ND | $5 \times 10^4$ | $9 \times 10^4$ |
| 36 | $6 \times 10^2$ | >$1 \times 10^5$ | $7 \times 10^5$ |
| 42 | ND | >$1 \times 10^6$ | $5 \times 10^6$ |
| 48 | $8 \times 10^4$ | >$1 \times 10^6$ | $5 \times 10^7$ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Figure 4:
FIG. 4. Detection of the FLAG epitope in cells infected with a transfectant virus. Antibody staining was used to identify the NA in MDCK cells infected with either PR8-WSN-FL79 (A, D) or A/WSN/33 wild-type virus (B, E), or on mock-infected MDCK cells (C, F). Nine hours after infection, cells were fixed with paraformaldehyde, treated with Triton X-100 and incubated with either anti-FLAG (A-C) or anti-WSN NA (D-F) monoclonal antibodies. Intensive Golgi staining (red) is apparent in positive samples (A, D, and E).

Recovery of influenza virus containing the FLAG epitope in the NA protein. To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPolI-WSN-NA/FL79) that contained a cDNA encoding both the NA protein and a FLAG epitope at the bottom of the protein's head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus (FIG. 4). Recovery of the PR8-WSN-FL79 virus was as efficient as that for the untagged wild-type virus (data not shown). These results indicate that the new reverse genetics system allows one to introduce mutations into the influenza A virus genome.

Figure 5:
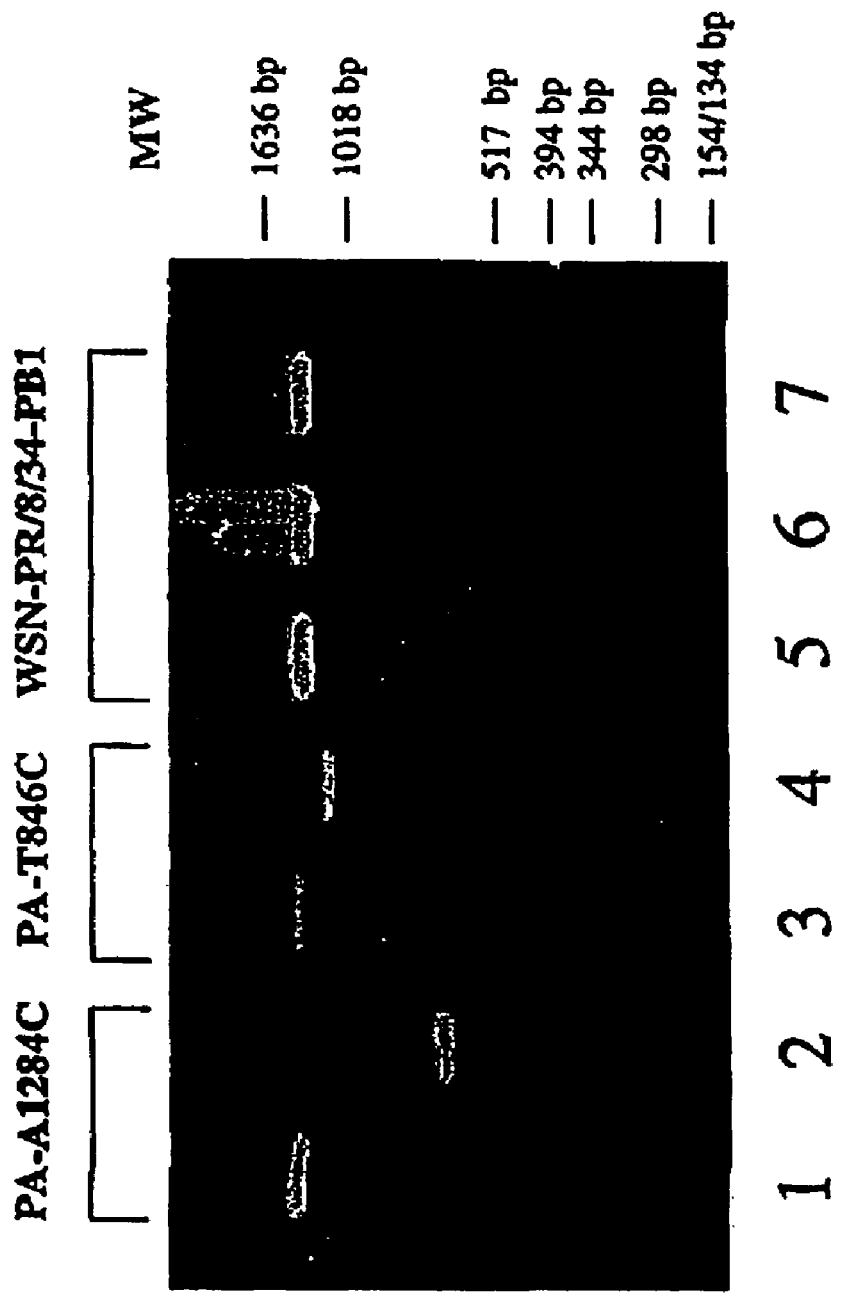
FIG. 5. Recovery of PA mutants. The PA gene of each virus was amplified by RT-PCR with primers that yield a 1226 bp fragment (position 677 to 1903 of the mRNA, lanes 1, 3, 5), which was then digested with the restriction enzyme Bsp120I (at position 846 of the mRNA, lanes 4, 7) or PvuII (at position 1284 of the mRNA, lanes 2, 6). The presence of Bsp120I or PvuII sites in the PCR products yielded either 169 bp and 1057 bp or 607 bp and 619 bp fragments, respectively. MW=molecular weight markers.

Generation of infectious influenza virus containing mutations in the PA gene. To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. As shown in FIG. 5, PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (Bunyaviridae family), but it contains only three segments of negative-sense RNA, and the efficiency of its production was low, $10^2$ pfU/$10^7$ cells. Although the virus yields differed among the experiments, consistently >$10^3$ pfu/106 cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991; Horimoto et al., 1994), NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. This advantage is demonstrated in FIG. 5, which the recovery of transfectant viruses with a mutated PA gene. Having the technology to introduce any viable mutation into the influenza A virus genome will enable investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel. & Piedra, 1998), leaving room for further improvement. One possibility would be to modify a cold-adapted vaccine with the reverse genetics system described above. Alternatively, one could start from scratch by using reverse genetics to produce a "master" influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family Orthomyxoviridae comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., Bunyaviridae, Arenaviridae). The ability to manipulate the viral genome without technical limitations has profound implications for the study of viral life cycles and their regulation, the function of viral proteins and the molecular mechanisms of viral pathogenicity.

EXAMPLE 2

Figure 7:
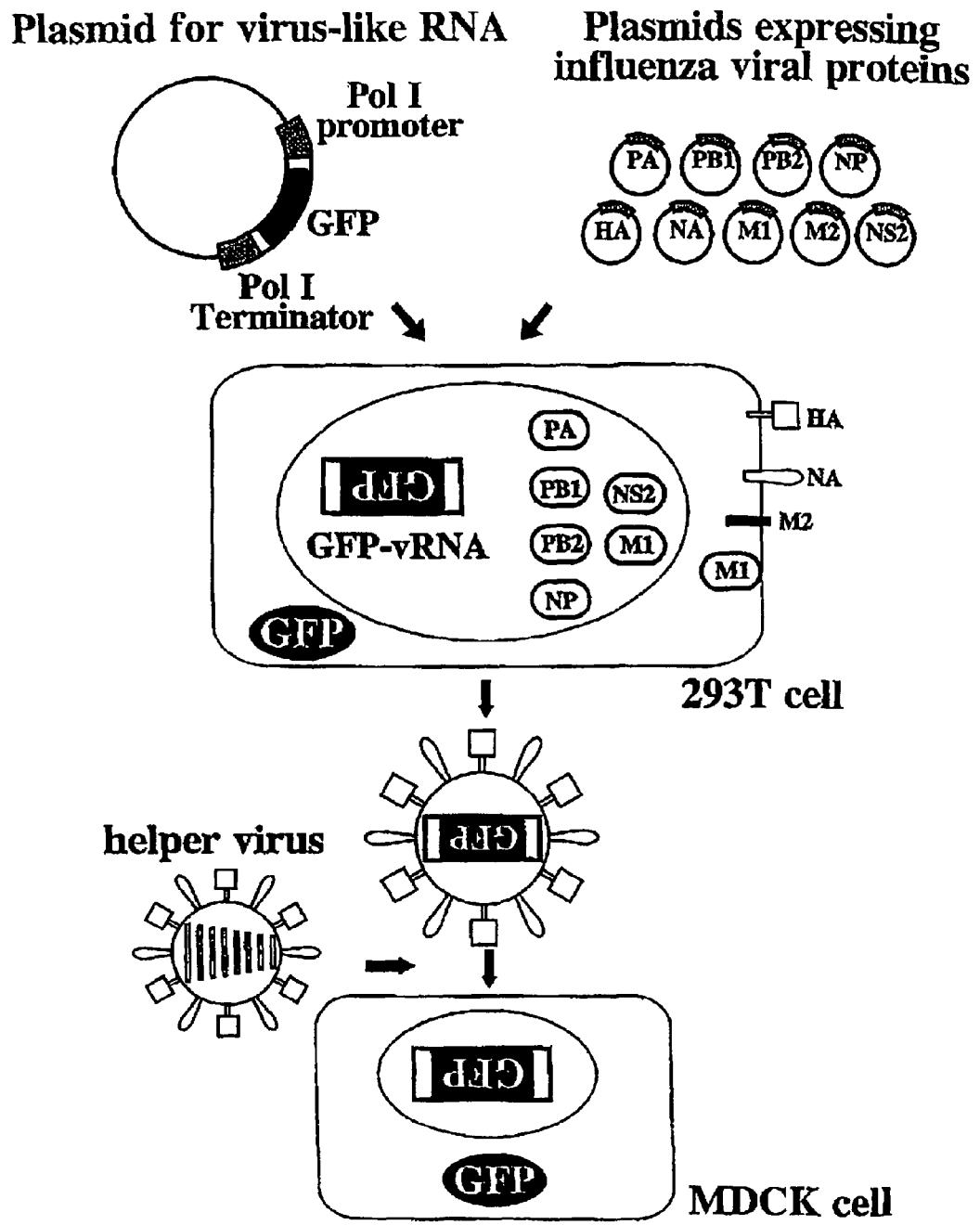
FIG. 7. The pPolI-GFP plasmid for generating influenza virus-like (VLP) RNA encoding the GFP protein. This plasmid contains the GFP gene (derived from pEGFP-N1; Clontech, Palo Alto, Calif.) in antisense orientation between the 5' and 3' noncoding regions of influenza A virus segment 5, flanked by the human RNA polymerase I promoter and the mouse RNA polymerase I terminator. Individual protein expression plasmids and a plasmid containing the RNA polymerase I promoter, a cDNA encoding the GFP reporter gene, and the RNA polymerase I terminator are transfected into 293T cells. Intracellular transcription by RNA polymerase I yields GFP vRNA of negative polarity, as indicated by inverted letters. Supernatants containing VLPs are harvested, mixed with influenza helper virus and inoculated into MDCK cells.

Expression of the influenza virus proteins PB2, PB1, PA, and NP leads to replication and transcription of an artificial viral RNA. To generate influenza VLPs, the RNA polymerase I system for the intracellular synthesis of influenza viral RNAs in vivo was employed (FIG. 7). In this system, a cDNA encoding a reporter gene in antisense orientation is flanked by the 5' and 3' noncoding regions of an influenza viral RNA. This cassette is inserted between an RNA polymerase I promoter and terminator. Transfection of such constructs into eukaryotic cells leads to transcription of the reporter gene by cellular RNA polymerase I, thereby generating influenza virus-like RNAs (Neumann et al., 1994). Upon influenza virus infection, the artificial vRNAs are replicated and transcribed by the viral polymerase complex, resulting in the expression of the reporter gene.

To determine whether expression of the PB2, PB1, PA, and NP proteins leads to expression of the reporter gene encoded by the RNA polymerase I-derived transcript, plasmids (1 μg each) expressing the NP protein of A/WSN/33 (H1N1) virus under control of the chicken β-actin promoter (pCAGGS-WSN-NP0/14), the polymerase proteins of A/PR/8/34 virus under control of the cytomegalovirus promoter [pcDNA762 (PB2), pcDNA774(PB 1), and pcDNA787(PA)], and an RNA polymerase I reporter gene construct (pPolI-GFP) were transfected into human embryonic kidney (293T) cells. Forty eight hours later, 30%-40% of the cells were expressing GFP (FIG. 8). In contrast, GFP expression could not be detected in transfected cells lacking the polymerase or NP proteins. These results indicated that NP and the three influenza viral polymerase proteins had formed a functional complex that replicated and transcribed the RNA polymerase I-derived GFP vRNA.

Optimal vRNA transcription and replication. To determine the amounts of plasmid DNA required for optimal reporter GFP expression, we modulated the expression of the polymerase proteins and NP. Previous studies had indicated that large amounts of PA reduce the extent of reporter gene expression in transcription/replication systems (Mena et al., 1996). Therefore, in a stepwise manner, the expression of PA from the plasmid was reduced, identifying 0.1 μg of pcDNA787(PA) as the template amount yielding the strongest expression of GFP. With NP, the major structural component of RNP complexes, high amounts of protein expression plasmid may be required. However, higher amounts of the plasmid did not appreciably affect the number of GFP-positive 293T cells. In addition, various amounts of the PB2 and PB1 protein expression plasmids (ranging from 1.0 to 0.03 μg) did not affect the GFP expression in 293T cells. Hence, in all subsequent experiments, 0.1 μg of pcDNA787 (PA), and 1.0 μg of pcDNA774(PB1), pcDNA762(PB2), and pCAGGS-WSN-NP0/14, was used.

Formation of influenza VLPs from cloned cDNAs. Previous studies with the vaccinia virus T7 RNA polymerase system showed that the formation of influenza VLPs requires nine influenza virus proteins: PB2, PB1, PA, HA, NA, NP, M1, M2, and NS2 (Mena et al., 1996). The NS1 protein, by contrast, is dispensable for particle formation (Mena et al., 1996). To establish an efficient plasmid-driven system for VLP generation, cDNAs were generated that encoded the HA, NA, M1, M2, and NS2 genes. The cDNAs were cloned into the eukaryotic expression vector pCAGGS/MCS (controlled by the chicken β-actin promoter), resulting in pEWSN-HA, pCAGGS-WNA15, pCAGGS-WSN-M1-2/1, pEP24c, and pCA-NS2, respectively. Expression of each protein was confirmed by Western blot analysis.

To generate VLPs, $10^6$ 293T cells were transfected with 1.0 μg of each protein expression plasmids (with the exception of pcDNA787(PA), for which 0.1 μg was employed), and with 1 μg of the reporter gene construct pPolI-GFP. Culture supernatants were harvested 48 hours after transfection and mixed with A/WSN/33 virus to provide the influenza virus proteins required for replication and transcription of GFP vRNA. The mixture was then inoculated into MDCK cells. Ten hours after incubation, GFP-positive MDCK cells were detected, corresponding to 450 particles/ml of supernatant (Table 3). Thus, plasmid-driven expression of all influenza viral structural proteins resulted in the formation of infectious influenza VLPs containing GFP vRNA. Moreover, GFP vRNA was delivered to MDCK cells.

Optimal assembly of influenza virus. VLP formation was also studied in cells expressing different amounts of the RNA polymerase I reporter gene construct, as well as HA, NA, M1, M2, and NS2 plasmid DNAs. In experiments with pPolI-GFP, 1.0 μg of the plasmid DNA was highly efficient in generating VLPs, whereas the efficiency was significantly reduced for 2.0 μg or 3.0 μg. Because the NS2 and M2 proteins are expressed in low amounts late in infection, it was likely that relatively small amounts of the expression plasmids would be needed for optimal VLP formation. Reduction of the M2 expression construct from 1.0 μg to 0.3 μg resulted in a more than tenfold increase in the number of GFP-positive MDCK cells (Table 3). Further reduction of plasmid to 0.03 μg did not increase the number of VLPs. For NS2, lower amounts of plasmid tested (0.1 μg) were associated with less efficient formation of VLPs (Table 3).

The M1 protein is the major structural component of the virion. Thus, high levels of M1 expression are likely required for efficient formation of VLPs. This prediction was tested in experiments comparing VLP formation in cells transfected with 1.0 μg or 2.0 μg of M1 plasmid DNA. As shown in Table 3, higher amounts of plasmid resulted in a more than tenfold increase in the number of GFP-positive MDCK cells. Comparison of two different amounts (1 μg vs. 2 μg) of plasmids expressing the HA and NA proteins did not reveal any appreciable differences in VLP formation, leading to selection of 1 μg of each plasmid (pEWSN-HA, pCAGGS-WNA15) for use in subsequent experiments. Overall, these studies resulted in a >100-fold increase in the efficiency of VLP formation, ultimately leading to the production of more than $10^4$ infectious influenza virus particles per ml of supernatant (FIG. 9).

TABLE 3

Optimal amounts of plasmid DNA for the formation of infectious VLPs.*

| Amount (μg) of plasmid DNA expressing: | | | | | | | | | | Relative efficiency of VLP formation† |
|---|---|---|---|---|---|---|---|---|---|---|
| PB2 | PB1 | PA | HA | NP | NA | M1 | M2 | NS2 | GFP vRNA | |
| 1.0 | 1.0 | 0.1 | 1.0 | 1.0 | 1.0 | 1.0 | 1.0 | 1.0 | 1.0 | 1 |
| 1.0 | 1.0 | 0.1 | 1.0 | 1.0 | 1.0 | 1.0 | 0.1 | 1.0 | 1.0 | 28 |
| 1.0 | 1.0 | 0.1 | 1.0 | 1.0 | 1.0 | 1.0 | 0.03 | 1.0 | 1.0 | 17 |
| 1.0 | 1.0 | 0.1 | 1.0 | 1.0 | 1.0 | 1.0 | 0.1 | 1.0 | 1.0 | 28 |
| 1.0 | 1.0 | 0.1 | 1.0 | 1.0 | 1.0 | 1.0 | 0.1 | 0.3 | 1.0 | 24 |
| 1.0 | 1.0 | 0.1 | 1.0 | 1.0 | 1.0 | 1.0 | 0.1 | 0.1 | 1.0 | 11 |
| 1.0 | 1.0 | 0.1 | 1.0 | 1.0 | 1.0 | 1.0 | 0.1 | 1.0 | 1.0 | 28 |
| 1.0 | 1.0 | 0.1 | 1.0 | 1.0 | 1.0 | 2.0 | 0.1 | 1.0 | 1.0 | 220 |

*293T cells were transfected with expression plasmids for all nine influenza virus structural proteins and with the RNA polymerase I-GFP gene plasmid. Forty-eight hours after transfection, VLP-containing supernatants were collected, mixed with A/WSN/33 helper virus, and inoculated into MDCK cells. The cells were fixed 10 h after infection and GFP expression was determined with a fluorescence microscope. Only the amounts of the M1, M2, and NS2 plasmids were varied (bold letter) to determine their optimal amounts for GFP expression in MDCK cells.
†The relative efficiency of VLP formation was determined by counting the number of GFP-positive cells in five microscopic fields. The sample containing 1 μg of each plasmid (which yielded 450 infectious VLP/ml of supernatant) was chosen as the reference (value of 1).

Authenticity of VLPs produced entirely from plasmids. To verify that VLPs initiate infection in the same manner as authentic influenza viruses, VLPs were neutralized with antibody to the WSN HA. VPL-containing supernatants derived from plasmid-transfected 293T cells were incubated with a pool of anti-WSN HA monoclonal antibodies or with a monoclonal antibody to the G protein of vesicular stomatitis virus (VSV) (negative control) for 1 hour at room temperature. A/PR/8/34 helper virus, which is not neutralized by the pool of anti-WSN HA monoclonal antibodies, was added to the mixture and inoculated into MDCK cells. Only the anti-WSN-HA-specific monoclonal antibody neutralized the VLPs, indicating that the HA medicates the attachment and entry of VLPs into cells.

Next, the minimal set of proteins required for the formation of VLPs was identified. Other have established that the three influenza virus polymerases and the NP are essential for the replication and transcription of vRNA (Honda et al., 1988). Therefore, each of these four proteins was included, but HA, NA, M1, M2, or NS2 was consecutively omitted. Exclusion of any of these plasmids did not affect the replication/transcription of GFP vRNA in transfected 293T cells. Supernatants derived from transfected 293T cells that lacked the HA, NA, M1, or NS2 protein did not promote GFP expression in infected MDCK cells, indicating the absence of infectious VLPs. Infectious VLPs were detected with omission of M2 but the number was low (>500 fold reduction compared to the full set of structural proteins). Thus, all influenza virus structural proteins are required for the efficient formation of infectious VLPs, in accord with data from studies of the vaccinia-virus system (Mena et al., 1996).

VSV glycoprotein can replace the HA and NA proteins in the production of VLPs. The influenza virus HA and NA proteins were replaced with the VSV G protein, which functions in receptor binding and fusion. In 293T cells transfected with pPolI-GFP; optimal amounts of the PB2, PB1, PA, NP, M1, M2, and NS2 expression constructs; and 1 μg of the VSV-G construct (PCAGGS-VSV-G), substitution of the VSV-G protein for influenza virus glycoproteins did not adversely affect VLP formation. To the contrary, higher numbers of GFP-positive cells were reproducibly found when VSV-G, rather than the HA and NA, served as the viral glycoprotein. Thus, the VSV G protein can be efficiently incorporated into influenza virions and can function as well as the HA and NA in virus release and entry.

An efficient system for generating infectious influenza virus particles would be an asset in research with this virus and potentially in the production of vaccines and vectors for gene therapy. In contrast to the extant vaccinia virus system, the VLP production strategy described here is highly efficient, both in the initial transfection of cells and in the yield of VLPs (>$10^4$ infectious particles/ml of supernatant). Moreover, it is driven entirely by plasmids expressing influenza virus proteins (i.e., in the absence of any other viral proteins), which greatly simplifies the interpretation of results. Another major advantage is the capability to study the effects of lethal mutations in virion formation, packaging of RNP complexes, budding of virus replication, and binding and fusion processes. In addition, it is likely that the system described hereinabove would operate equally well with other viruses, e.g., paramyxoviruses and rhabdoviruses.

Influenza virus HA and NA proteins can be functionally replaced by the VSV glycoprotein G. Previously, it had been reported that influenza viruses failed to incorporate VSV G protein when provided by recombinant SV40 virus (Naim et al., 1993). The results described herein suggest that neither the HA nor the NA is essential for the formation of VLPs, although it cannot be ruled out that these glycoproteins play a role in interactions with other viral proteins, thus affecting the structure of virions, as suggested by the elongated shapes of viruses expressing tail-less HAs, NAs, or both (Garcia-Sastre et al., 1995; Jin et al., 1994; Jin et al., 1997; Mitnaul et al., 1996).

The plasmid-based system described hereinabove may be particularly useful for therapeutic gene delivery. VLPs can be prepared that contain the vRNA encoding the proteins required for transcription and replication (i.e., the NP and the polymerases), as well as a vRNA encoding the protein of interest. These particles are infectious and can deliver a designated gene into target cells, where it would replicate and be transcribed. Because these particles do not contain a complete complement of viral genes, they can not produce infectious progeny viruses. This feature, together with the lack of integration of the viral genome into host chromosomes, would ensure the biological safety of gene delivery in human and nonhuman subjects. Finally, the availability of 15 HA and 9 NA subtypes and their variants would allow the repeated administration of VLPs, thereby overcoming immunoresistance to vector-generated proteins, one of the major obstacles faced with repeated use of other viral vectors, such as adenoviruses. A further benefit of the plasmid-driven system would be realized in situations requiring only short-term expression of foreign proteins, as in cancer treatment.

EXAMPLE 3

Figure 10:
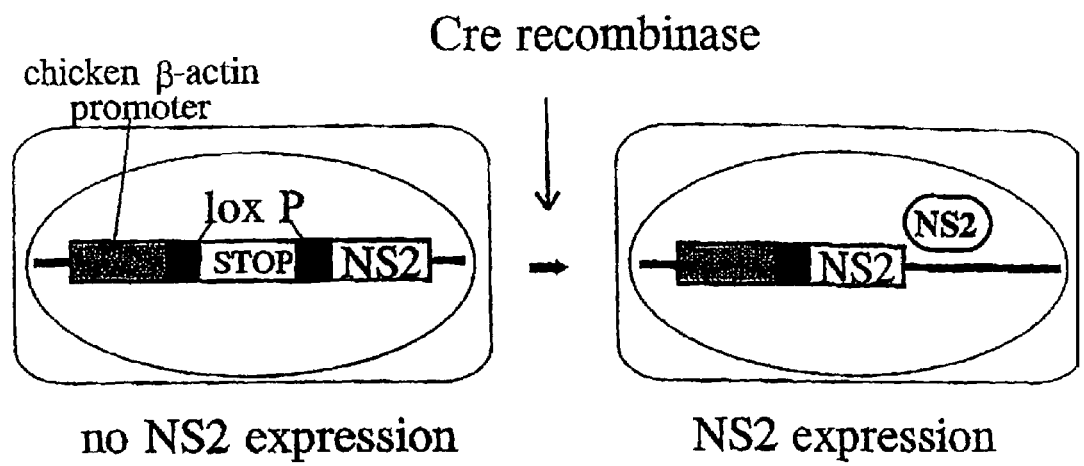
FIG. 10. Schematic of the use of Cre recombinase to express influenza NS2 protein in a cell, the genome of which is augmented with a recombinant DNA molecule. The genome of the cell comprises a recombinant DNA molecule which comprises a promoter linked to a site specific recombination site (e.g., 1oxP) linked to a transcription stop sequence linked to a second site specific recombination site in the same orientation as the first site specific recombination site linked to the NS2 gene.
Figure 11:
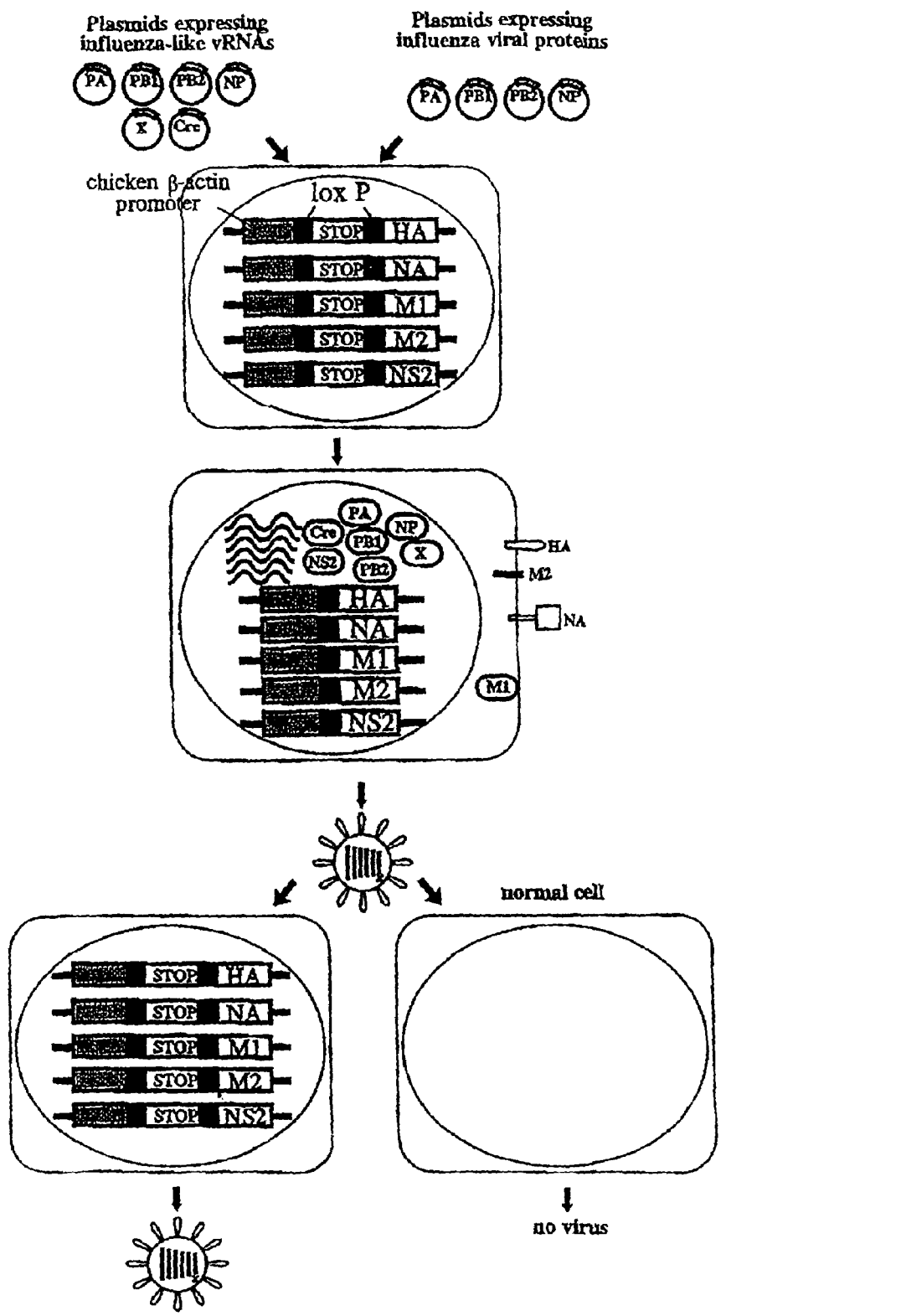
FIG. 11. Preparation of replication defective influenza virus.

By using the Cre-loxP system, one can generate packaging cell lines for the production of replication-defective viruses. For example, a protein expression vector is prepared that contains a transcription stop cassette (e.g., pBS302 of Life Technologies, Bethesda, Md.; and Sauer et al., 1993; Lasko et al., 1992; Pichel et al., 1993; Bolivar et al., 1977; Stuhl et al., 1981; Stuhl, 1985; Fiers et al., 1978), flanked by two loxP sites, and one of the viral genes. Transcription, initiated at the promoter sequence, is blocked at the transcription stop sites. Thus, the viral gene is not transcribed and translated. A cell that is stably transfected with such a vector is infected with an influenza virus that lacks the vRNA encoding the gene cloned into the loxP system. This virus also contains an additional vRNA encoding the Cre protein. This virus is not viable in normal cells, because it lacks one of its vRNAs. However, in the packaging cell line, the Cre protein which is expressed from the vRNA results in recombination at the loxP site, resulting in the deletion of the transcription stop site. Thus, the respective viral gene(s) is now transcribed and expressed, allowing the virus to amplify in these cells (FIG. 10).

Figure 12:
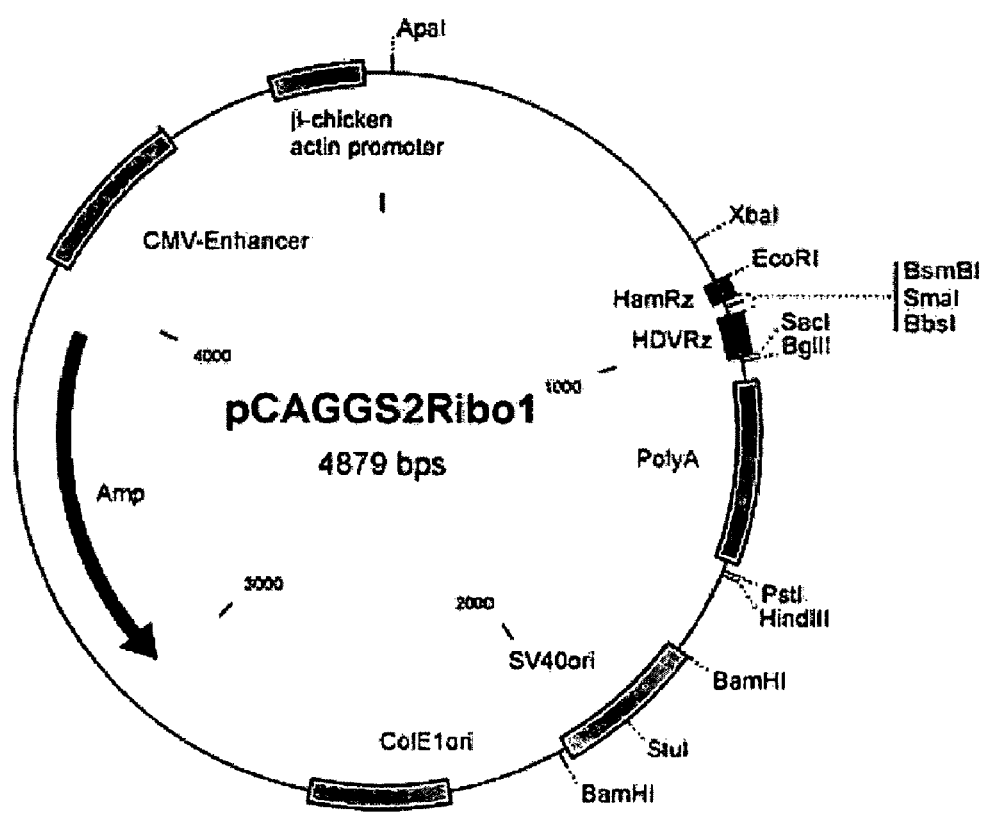
FIG. 12. Vector map of pCAGGS-2Ribo-1. In vertebrate cells, RNA polymerase II drives RNA transcription of the double ribozyme cassette, which is under the control of the strong chicken β-actin promoter/CMV enhancer cassette. Viral cDNA is cloned downstream of the hammerhead ribozyme site (HamRz) and upstream of the HDV ribozyme site (HDVRz).

In addition, packaging cell lines are prepared that express the late viral proteins (i.e., HA, NA, M1, M2, and NS2) controlled by the loxP system (FIG. 12). The HA and NA can be replaced by other viral receptor-binding and fusion proteins (e.g., Ebola GP, Marburg GP, Bunyaviridae glycoproteins GP1 and GP2, the G and/or F proteins of rhabdovirus and paramyxovirus, thogotovirus glycoprotein, and the glycoproteins of positive-strand RNA viruses). Virus-like particles are generated which contain the vRNAs encoding the proteins required for replication/transcription (i.e., the polymerase and NP proteins), a vRNA encoding the gene of interest, and a vRNA encoding Cre. These vRNAs are packaged into virus-like particles in the packaging cell lines.

These virus-like particles can be used for vaccine and gene therapy purposes because (i) they do not contain the full complement of viral genes and thus no infectious progeny particles can be formed, meeting the stringent safety concerns; (ii) they will likely express the foreign protein at high levels; (iii) they do not express the viral glycoproteins (HA, NA) that are the major antigens; thus, the host immune response against the viral proteins should be limited.

EXAMPLE 4

A RNA polymerase II/double ribozyme system was established that can lead to the generation of influenza virus, e.g., influenza A virus, influenza B virus or influenza C virus, in any vertebrate cell line, e.g., human 293T cells, murine NA cells or hamster BHK-21 cells. An influenza A vRNA was expressed, and an influenza A virus was generated, containing a segment (PB2) derived from an RNA transcript by RNA polymerase II.

Materials and Methods

Cells 293T human embryonic kidney cells, a derivative of the 293 line constitutively expressing the gene for the simian virus 40 T antigen (DuBridge et al., 1989), were maintained in DMEM (glucose concentration: 4.5 g/l) supplemented with 10% FCS, 4 mM L-glutamine, and antibiotics. Madin-Darby canine kidney cells (MDCK) were grown in minimum essential medium with Eagle's salts (MEM) containing 5% newborn calf serum, 4 mM L-glutamine and antibiotics.

Plasmid Construction

The construction of the RNA polymerase II driven vRNA expression vector was based on pCAGGS-MCS (Hatta et al., 2001; Niwa et al., 1991) in which RNA polymerase II mediated transcription is driven by a β-actin chicken promoter/CMV enhancer cassette. The HDVRz cassette was amplified from pX8dT (Schnell et al., 1984) using the primers 5'-GCATGCGAAGACTTGGGTCGGCATG-GCATCTCCACCTCCT-3' (SEQ ID NO:17) and 5'-AG-ATCTAGGGAGCTCTCCCTTAGCCATCCGA-3' (SEQ ID NO:18) and cloned into pCAGGS-MCS using BglII and SphI restriction sites. The HamRz cassette was created by an oligolinker ligation with 5'-AATTCTTTCTACTCTGAT-GAGTCCGTGAGGACGAAACCCGGAGTCCC GGGTC-GGAGACGATGCA-3' (SEQ ID NO:19) and 5'-TCGTCTC-CGACCCGGGACTCCGGGTTTCGTCCTCACGGACTC-ATCAGA GTAGAAAG-3' (SEQ ID NO:20) using EcoRI and NsiI sites in pCAGGS-MCS. Digestion of the resulting PolII/double ribozyme vector pCAGGS-2Ribo-1 (FIG. 12) with BbsI and BsmBI yielded a linearized vector for insertion of a viral cDNA construct obtained by PCR amplification with 5'-CGTCTCCGGTCAGTAGAAACAAGG-3' (SEQ ID NO:21) and 5'-CGTCTCCACCCAGCAAAAGCAGG-3' (SEQ ID NO:22). RNA polymerase II driven expression and subsequent autocatalytic cleavage of the two ribozymes at the 5' and the 3' termini result in an influenza A vRNA molecule with authentic 3' and 5' ends (FIG. 13). pCAGGS-2Ribo-PB2/483-627E expressed the PB2 vRNA of HK483 containing a single Lys-to-Glu substitution at amino acid position 627.

Generation of Recombinant Virus

Generation of the recombinant influenza A virus A/WSN/33 and HK3/PB2-627E based exclusively on the RNA polymerase I reverse genetics system was described by Neumann et al. (1999) and Hatta et al. (2001), respectively.

To generate HK3/PB2-627E (FIG. 14) or WSN/HK483 PB2 627E (FIG. 14), 293T cells were transfected with pCAGGS-2Ribo-PB2/483-627E (0.1 µg, for the production of the PB2 segment) together with plasmids for the production of the remaining RNA segments of respective viruses by RNA polymerase I (0.1 µg each, pPolI plasmids). These cells were also transfected with protein expression constructs for PA, PB1, PB2 and NP of WSN/33 (1 µg each). Forty-eight hours after transfection, aliquots of the 293T cell supernatants were collected and virus was amplified in MDCK cells or titrated on MDCK cells by a plaque assay. For further analysis of the recombinant virus, viral RNA was extracted from viral supernatant and PB2 vRNA was analyzed by RT-PCR and sequencing reactions. As a negative control, the vRNA expression construct for PB2 was omitted from the transfection mixture, and the use of a RNA polymerase I expression construct for PB2 vRNA, instead of pCAGGS-2Ribo-PB2/483-627E, served as a positive control.

Results

Figure 13:
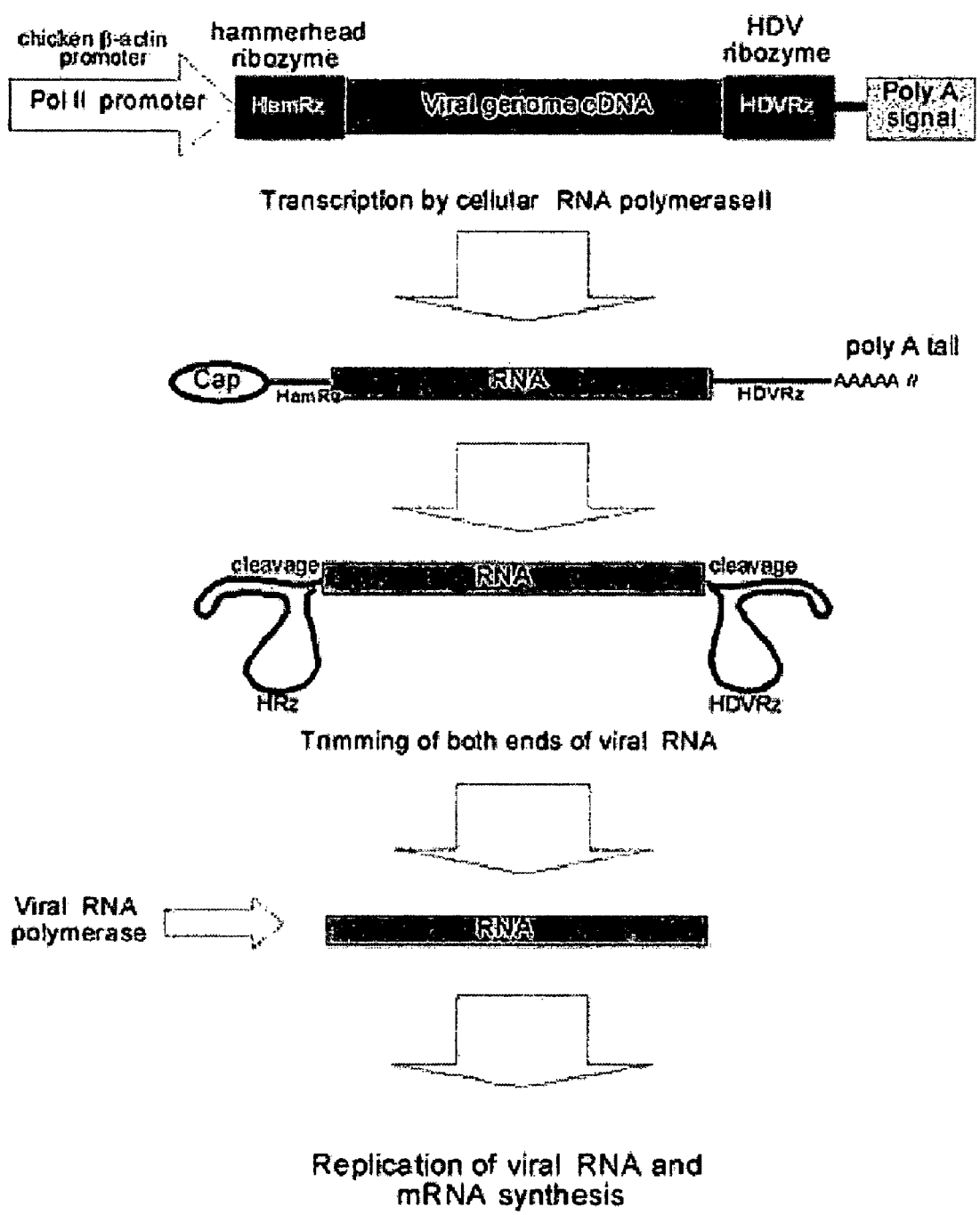
FIG. 13. Schematic diagram of the RNA polymerase II/double ribozyme system to generate full-length vRNA for reverse genetics. The primary mRNA transcript, generated by RNA polymerase II, includes a vRNA flanked by two ribozyme sites (HamRz and HDVRz). Autocatalytic cleavage by the ribozymes results in a vRNA with authentic 5' and 3' ends, which serves as a template in viral transcription and replication.

For the synthesis of full-length influenza A vRNAs with authentic 5' and 3' ends, pCAGGS-2Ribo-1 was construct (FIG. 12). cDNAs derived from full length viral RNAs were then inserted so that they are flanked at the 5' end by a HRz and at the 3' end by a HDVRz sequence. The expression of this double ribozyme cassette is controlled upstream by the chicken β-actin promoter/CMV enhancer cassette. Upon transfection of such a construct into cells, the double ribozyme cassette, including the viral sequences, is transcribed by cellular RNA polymerase II, and autocatalytic ribozyme cleavage at both termini of the transcript results in the generation of authentic vRNA (FIG. 13).

Figure 14:
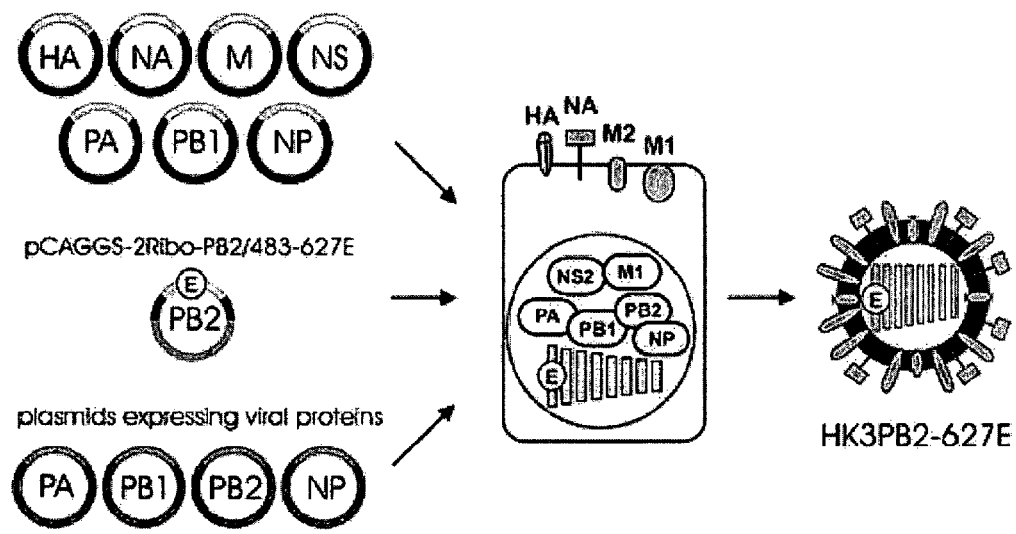
FIG. 14. Generation of HK3PB2-627E virus from cloned cDNAs. PA, PB1, NP, M, NS, NA, and HA vRNAs of HK3/PB2-627E are synthesized by an RNA polymerase I system, whereas PB2 vRNA is provided by the RNA polymerase II/double ribozyme system. The viral NP and polymerase proteins, expressed by protein expression constructs, replicate and transcribe the vRNAs, resulting in the synthesis of all viral proteins and the generation of replicating influenza virus.

To test the feasibility of this approach the plasmid pCAGGS-2Ribo-PB2/483-627E was constructed. This construct encodes PB2 vRNA of HK3/PB2-627E containing Glu at amino acid position 627 between the two ribozyme sites. This construct was tested in a reverse genetics approach by coexpression of 12 plasmids in 293T cells: PB2 vRNA was expressed by pCAGGS-2Ribo-PB2/483-627E, and the remaining vRNAs of HK3/PB2-627E (PA, PB1, NP, M, NS, NA, HA) by the RNA polymerase I system; protein expression plasmids provided PA, PB1, PB2 and NP of A/WSN/33 (FIG. 14). As a negative control, the vRNA expression construct for PB2 was omitted from the transfection mixture, and as a positive control, pCAGGS-2Ribo-PB2/483-627E was replaced by a RNA polymerase I expression construct for PB2 vRNA (pPoII-PB2/483-627E). Forty eight hours after transfection, aliquots of 293T cell supernatants were incubated with MDCK cells. Within forty eight hours, a cytopathic effect (CPE) was observed for supernatants derived from 293T cells transfected with pCAGGS-2Ribo-PB2/483-627E or pPoII-PB2/483-627E, indicating the generation of influenza virus in these cells. No CPE was seen in the absence of a PB2 vRNA expressing plasmid. To prove that influenza virions were indeed generated with a combination of RNA polymerase I and RNA polymerase I/double ribozyme constructs expressing influenza vRNAs, vRNA was isolated from the MDCK cell supernatant and the PB2 RT-PCR product sequenced at amino acid position 627. The recombinant virus indeed contained the PB2 gene encoded by pCAGGS-2Ribo-PB2/483-627E.

To further prove the functionality of the RNA polymerase I/double ribozyme system, 293T cells were transfected with pCAGGS-2Ribo-PB2/483-627E for the production of PB2 vRNA of HK3/PB2-627E and pPolI plasmids for the production of PA, PB1, NP, M, NS, NA, HA vRNAs of A/WSN/33 together with plasmids for the protein expression of PA, PB1, PB2 and NP of A/WSN/33 (FIG. 15). $5\times10^3$ pfu/ml of virus was found in the supernatant of 293T cells 48 hours post transfection, similar to what was observed in the positive control when all vRNAs including PB2 vRNA were expressed by pPolI plasmids.

Discussion

This study demonstrates that an RNA polymerase II/double ribozyme system can generate influenza A vRNAs with authentic 5' and 3' ends. In this system, the strong chicken β-actin promoter/CMS enhancer cassette drives the expression of an RNA transcript encoding an influenza A vRNA which is flanked by ribozyme sequences at the 5' end (HRz) and the 3' end (HDVRz) of the vRNA. The autocatalytic cleavage of this primary RNA transcript at the ribozyme sites resulted in generation of influenza A vRNAs.

Using this system, recombinant influenza A virus was generated that possessed PB2 vRNA derived from the RNA polymerase II/double ribozyme system. Thus, this experiment clearly proves the functionality of the influenza A vRNA molecules generated by the RNA polymerase II/double ribozyme system, indicating that the RNA polymerase II/double ribozyme system should allow generation of influenza A virus and/or other segmented RNA viruses entirely from cloned cDNA.

The new RNA polymerase II/double ribozyme system provides several major advantages over the two reverse genetic systems for negative strand RNA viruses described so far. The RNA polymerase II promoter has no host cell specificity. Thus, this RNA polymerase II/double ribozyme reverse genetics system can be used in any vertebrate cell line. In contrast, RNA polymerase I is host-specific: human RNA polymerase I failed to initiate transcription from the mouse promoter and vice versa (Grummt et al., 1982; Learned et al., 1982). In addition, compared to the T7 polymerase system, the RNA polymerase II/double ribozyme system provides the advantages of not requiring the expression of a RNA polymerase in trans and precise trimming of viral RNA termini. For many viruses the synthesis of the exact 3' end of the viral RNA genome is crucial for efficient virus generation. In the T7 RNA polymerase system, however, the addition of one to three G nucleotides is necessary for efficient transcription, which in many cases reduces the efficiency of triggering viral replication and therefore the generation of recombinant virus by reverse genetics. The RNA polymerase II/double ribozyme system synthesizes RNA molecules with termini identical to the authentic viral RNAs.

In conclusion, the ability of a RNA polymerase II/double ribozyme system to artificially synthesize an authentic influenza A vRNA was shown. This is the first description of the generation of a segmented negative-strand RNA virus possessing an RNA segment derived from a RNA polymerase II based reverse genetics system. Since the RNA polymerase II/double ribozyme system is not subject to restrictions with respect to host cell species, it will likely have a great impact on vaccine production, where due to biosafety precautions, only a very limited number of cell lines can be used. Chicken embryonic fibroblasts are likely to be approved for the production of live vaccines; therefore candidate strains in these cells are generated by reverse genetics. Because the human RNA polymerase I promoter is not functional in chicken embryonic fibroblasts (data not shown), a reverse genetics system based on RNA polymerase I will not be successful in this system. The RNA polymerase II/double ribozyme system will likely overcome these limitations and provide the basis for the broad use of a reverse genetics system for vaccine production for influenza and other negative-stranded RNA viruses.

REFERENCES

Albo et al., *J. Virol.,* 70:9013 (1996).

*Avery's Drug Treatment: Principles and Practice of Clinical Pharmacology and Therapeutics,* 3rd edition, ADIS Press, Ltd., Williams and Wilkins, Baltimore, Md. (1987).

Aymard-Henry et al., *Virology: A Practical Approach, Oxford IRL Press, Oxford,* 119-150 (1985).

Bachmeyer, *Intervirology,* 5:260 (1975).

Berkow et al., eds., *The Merck Manual,* 16th edition, Merck & Co., Rahway, N.J. (1992).

Baron et al., *J. Virol.,* 71:1265 (1997).

Bolivar et al., *Gene,* 2:95 (1977).

Bridgen et al., *Proc. Natl. Acad. Sci. U.S.A,* 93:15400 (1996).

Castrucci et al., *J. Virol.,* 66:4647 (1992).

Castrucci et al., *J. Virol.,* 69:2725 (1995).

Chowira et al., *J. Biol. Chem.,* 269:25856 (1994).

Collins et al., *Proc. Natl. Acad. Sci. U.S.A.,* 92:11563 (1995).

Conzelmann et al., *J. Gen. Virol.,* 77:381 (1996).

Conzelmann et al., *Trends Microbiol.,* 4:386 (1996).

Conzelmann, *Annu. Rev. Genet.,* 32:123 (1998).

Cozelmann et al., *J. Virol.,* 68:713 (1994).

DuBridge et al., *Mol. Cell Biol.,* 7:379 (1987).

Dunn et al., *Virology,* 211:133 (1995).

Edwards, *J. Infect. Dis.,* 169: 68 (1994).

Elliott, *Mol. Med.,* 3:572 (1997).

Enami et al., *J. Virol.* 65:2711 (1991).

Enami et al., *Proc. Natl. Acad. Sci. U.S.A.,* 87:3802 (1990).

Enami et al., *Virology,* 185:291 (1991).

Fiers et al., *Nature,* 273:113 (1978).

Fodor et al., *J. Virol.,* 73:9679 (1999).

Garcia-Sastre et al., *Virus Res.,* 37:37 (1995).

Garcin et al., *EMBO J.,* 14:6087 (1995).

Goto et al., *Virology,* 238:265 (1997).

Grand and Skehel, *Nature, New Biology,* 238:145 (1972).

Grummt et al., *Nature,* 296:173 (1982).

Hagen et al., *J. Virol.,* 68:1509 (1994).

Hatta et al., *Science,* 293:1840 (2001).

He et al., *Virology,* 237:249 (1997).

Hoffman et al., *J. Virol.,* 71:4272 (1997).

Honda et al., *J. Biochem.* (Tokyo), 104:1021 (1988).
Horimoto et al., *J. Virol.*, 68:3120 (1994).
Huddleston et al., *Nucl. Acids Res.*, 10:1029 (1982).
Inoue et al., *J. Virol. Methods*, 107:229 (2003).
Jin et al., *EMBO J.*, 13:5504 (1994).
Jin et al., *EMBO J.*, 16:1236 (1997).
Kajima et al., *Pharma Ther.*, 68:247 (1995).
Kato et al., *Genes Cells*, 1:569 (1996).
Keitel et al., in *Textbook of Influenza*, eds. Nickolson, K. G., Webster, R. G., and Hay, A. (Blackwell, Oxford), pp. 373-390 (1998).
Kilbourne, Bull. M2 World Health Org., 41: 653 (1969).
Kobasa et al., *J. Virol.*, 71:6706 (1997).
Kovesdi et al., *J. Curr. Opin. Biotechnol.*, 8:583 (1997).
Kumar et al., *FASEB J.*, 9:1183 (1995).
Lasko et al., *Proc. Natl. Acad. Sci. USA*, 89:6232 (1992).
Layer & Webster, *Virology*, 69:511 (1976).
Lawson et al., *Proc. Natl. Acad. Sci. U.S.A.*, 92:4477 (1995).
Leahy et al., *J. Virol.*, 71:8347 (1997).
Leahy et al., *J. Virol.*, 71:8352 (1997).
Leahy et al., *J. Virol.*, 72:2305 (1998).
Learned et al., *J. Mol. Appl. Genet.*, 1:575 (1982).
Li et al., *Virus Res.*, 37:153 (1995).
Luytjes et al., *Cell*, 59:1107 (1989).
Marriott et al., *Adv. Virus Res.*, 53:321 (1999).
Mena et al., *J. Virol.*, 70:5016 (1996).
Mizrahi, (ed.), *Viral Vaccines*, Wiley-Liss, New York, 39-67 (1990).
Murphy, *Infect. Dis. Clin. Pract.*, 2: 174 (1993).
Muster et al., *Proc. Natl. Acad. Sci. USA*, 88: 5177 (1991).
Munoz et al., *Antiviral Res.*, 46:91 (2000).
Nagai et al., *Microbiol. Immunol.*, 43:613 (1999).
Nagai, *Rev. Med. Virol.*, 9:83 (1999).
Naim et al., *J. Virol.*, 67:4831 (1993).
Neumann et al., *Adv. Virus Res.*, 53:265 (1999).
Neumann et al., *J. Gen. Virol.*, 83:2635 (2002).
Neumann et al., *J. Virol.*, 71:9690 (1997).
Neumann et al., *Proc. Natl. Acad. Sci. U.S.A*, 96:9345 (1999).
Neumann et al., *Virology*, 202:477 (1994).
Neumann et al., *Virology*, 287:243 (2001).
Niwa et al., *Gene*, 108:193 (1991).
Ogra et al., *J. Infect. Dis.*, 134: 499 (1977).
Osol (ed.), *Remington's Pharmaceutical Sciences*, Mack Publishing Co., Easton, Pa. 1324-1341 (1980).
Palese et al., *Proc. Natl. Acad. Sci. U.S.A.*, 93:11354 (1996).
Parks et al., *J. Virol.*, 73:3560 (1999).
Pekosz et al., *Proc. Natl. Acad. Sci. U.S.A*, 96:8804 (1999).
Perez et al., *Virology*, 24:52 (1998).
Pichel et al., *Oncogene*, 8:3333 (1993).
Pleschka et al., *J. Virol.*, 70:4188 (1996).
Pley et al., *Nature*, 372:68 (1994).
Radecke et al., *EMBO J.*, 14:5773 (1995).
Radecke et al., *Virology*, 217:418 (1996).
Roberts et al., *Virology*, 247:1 (1998).
Robertson et al., *Biologicals*, 20:213 (1992).
Robertson et al., *Giornale di Igiene e Medicina Preventiva*, 29:4 (1988).
Rose, *Proc. Natl. Acad. Sci. U.S.A*, 93:14998 (1996).
Schnell et al., *EMBO J.*, 13:4195 (1994).
Struhl et al., *J. Mol. Biol.*, 152:553 (1985).
Struhl, *NAR*, 13:8587 (1985).
Subbarao et al., *J. Virol.*, 67:7223 (1993).
Weber et al., *Arch. Virol.*, 142:1029 (1997).
Weber et al., *J. Virol.*, 70:8361 (1996).
Weber et al., *Arch. Virol*, 142:1029 (1997).
World Health Organization TSR No. 673 (1982).
Whelan et al., *Proc. Natl. Acad. Sci. U.S.A.*, 92:8388 (1995).
Yasuda et al., *J. Virol.*, 68:8141 (1994).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition comprising a plurality of vectors, comprising a) vectors for vRNA production including a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein at least one vector comprises a RNA polymerase II promoter 5' to a first ribozyme sequence which is 5' to the viral cDNA which is 5' to a second ribozyme sequence which is 5' to the transcription termination sequence, wherein any vector for vRNA production which does not have a RNA polymerase II promoter, has a RNA polymerase I promoter; and b) vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, or a vector comprising a promoter operably linked to a DNA segment encoding influenza virus NP; and wherein transcription from the RNA polymerase II promoter of the at least one vector comprising the RNA polymerase II promoter 5' to a first ribozyme sequence which is 5' to the viral cDNA which is 5' to a second ribozyme sequence which is 5' to the transcription termination sequence, results in a transcript that is a template for influenza virus polymerase, and wherein transfection of a vertebrate cell with the plurality of vectors yields infectious influenza virus.

2. The composition of claim 1 wherein the vectors of b) further include a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2.

3. A composition comprising a plurality of vectors, comprising a) vectors for vRNA production including a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus cDNA for NB and NA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein at least one vector comprises a RNA polymerase II promoter 5' to a first ribozyme sequence which is 5' to the viral cDNA which is 5' to a second ribozyme sequence which is 5' to the transcription termination sequence, wherein any vector for vRNA production which does not have a RNA polymerase II promoter, has a RNA polymerase I promoter; and b) vectors for vRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, or a vector comprising a promoter operably linked to a DNA segment encoding influenza virus NP; and wherein transcription from the RNA polymerase II promoter of the at least one vector comprising the RNA polymerase II promoter 5' to a first ribozyme sequence which is 5' to the viral cDNA which is 5' to a second ribozyme sequence which is 5' to the transcription termination sequence, results in a transcript that is a template for influenza virus polymerase, and wherein transfection of a vertebrate cell with the plurality of vectors yields infectious influenza virus.

4. The composition of claim 3 wherein the vectors of b) further include a vector comprising a promoter operably linked to a DNA segment encoding influenza virus NP, a vector comprising a promoter operably linked to a DNA segment encoding influenza virus HA, a vector comprising a promoter operably linked to a DNA segment encoding influenza virus NA and NB, a vector comprising a promoter operably linked to a DNA segment encoding influenza virus M, or a vector comprising a promoter operably linked to a DNA segment encoding influenza virus NS2.

5. The composition of claim 1 or 3 wherein the HA is a type A HA.

6. The composition of claim 1 or 3 wherein the HA is a type B HA.

7. The composition of claim 1 or 3 wherein a plurality of the vectors of a) comprise a RNA polymerase II promoter.

8. The composition of claim 1 or 3 wherein all of the vectors of a) comprise a RNA polymerase II promoter.

9. The composition of claim 1 or 3 wherein each vector of a) is on a separate plasmid.

10. The composition of claim 1 or 3 wherein each vector of b) is on a separate plasmid.

11. The composition of claim 1 or 3 wherein the RNA polymerase I promoter is a human RNA polymerase I promoter.

12. The composition of claim 1 or 3 wherein the each of the vectors of b) further comprise a RNA transcription termination sequence.

13. The composition of claim 1 or 3 wherein the transcription termination sequence of vRNA vectors that do not comprise the RNA polymerase II promoter, is a RNA polymerase I transcription termination sequence or a ribozyme.

14. The composition of claim 1 or 3 further comprising a vector comprising a promoter linked to 5' influenza virus sequences comprising 5' influenza virus noncoding sequences linked to a cDNA of interest linked to 3' influenza virus sequences comprising 3' influenza virus noncoding sequences linked to a transcription termination sequence.

15. The composition of claim 14 wherein the cDNA of interest is in the sense orientation.

16. The composition of claim 14 wherein the cDNA of interest is in the antisense orientation.

17. The composition of claim 14 wherein the cDNA of interest comprises an open reading frame encodes an immunogenic polypeptide or peptide of a pathogen or a therapeutic polypeptide or peptide.

18. The composition of claim 1 or 3 further comprising a vector comprising a RNA polymerase II promoter linked to a first ribozyme sequence linked to 5' influenza virus sequences comprising 5' influenza virus noncoding sequences linked to the cDNA of interest linked to 3' influenza virus sequences comprising 3' influenza virus noncoding sequences linked to a second ribozyme sequence linked to a transcription termination sequence.

19. The composition of claim 18 wherein the cDNA of interest comprises an open reading frame encodes an immunogenic polypeptide or peptide of a pathogen or a therapeutic polypeptide or peptide.

20. A method to prepare influenza virus, comprising: contacting a cell with the composition of claim 1 or 3 in an amount effective to yield infectious influenza virus.

21. The method of claim 20 further comprising isolating the virus.

22. A method to prepare a gene delivery vehicle, comprising: contacting cells with the composition of claim 14 or 18 in an amount effective to yield influenza virus, and isolating the virus.

23. A cell contacted with the composition of claim 1 or 3.

24. A method to prepare influenza virus, comprising contacting a vertebrate cell with a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising a promoter operably linked to an influenza virus NP cDNA linked to a transcription termination sequence, a vector for vRNA production comprising a promoter operably linked to an influenza virus NA cDNA linked to a transcription termination sequence, a vector for vRNA production comprising a promoter operably linked to an influenza virus M cDNA linked to a transcription termination sequence, and a vector for vRNA production comprising a promoter operably linked to an influenza virus NS cDNA linked to a transcription termination sequence, a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, so as to yield infectious virus, wherein the promoter in at least one vector for vRNA production comprising a viral cDNA comprises a RNA polymerase II promoter 5' to a first ribozyme sequence which is 5' to the viral cDNA which is 5' to a second ribozyme sequence which is 5' to a transcription termination sequence, wherein any vector for vRNA production which does not have a RNA polymerase II promoter, has a RNA polymerase I promoter; and wherein transcription from the RNA polymerase II promoter of the at least one vector comprising the RNA polymerase II promoter 5' to a first ribozyme sequence which is 5' to the viral cDNA which is 5' to a second ribozyme sequence which is 5' to the transcription termination sequence, results in a transcript that is a template for influenza virus polymerase.

25. The method of claim 24 further comprising contacting the cell with a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, and a vector comprising a promoter operably linked to a DNA segment encoding influenza virus NS2.

26. A method to prepare influenza virus, comprising contacting a vertebrate cell with a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising promoter operably linked to an influenza virus NP cDNA linked to a transcription termination sequence, a vector for vRNA production comprising a promoter operably linked to an influenza virus cDNA for NB and NA linked to a transcription termination sequence, a vector for vRNA production comprising a promoter operably linked to an influenza virus M cDNA linked to a transcription termination sequence, a vector for vRNA production comprising a promoter operably linked to an influenza virus NS cDNA linked to a transcription termination sequence, a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, a vector for mRNA production comprising a promoter operably linked to a DNA segment encoding influenza virus NP, wherein at least one vector for vRNA production comprises a RNA polymerase II promoter 5' to a first ribozyme sequence which is 5' to the viral cDNA which is 5' to a second ribozyme sequence which is 5' to the transcription termination sequence, wherein any vector for vRNA production which does not have a RNA polymerase II promoter, has a RNA polymerase I promoter; and wherein transcription from the RNA polymerase II promoter of the at least one vector comprising the RNA polymerase II promoter 5' to a first ribozyme sequence which is 5' to the viral cDNA which is 5' to a second ribozyme sequence which is 5' to the transcription termination sequence, results in a transcript that is a template for influenza virus polymerase.

27. The method of claim 26 further comprising contacting the cell with a vector comprising a promoter operably linked to a DNA segment encoding influenza virus HA, a vector comprising a promoter operably linked to a DNA segment encoding influenza virus NA and NB, a vector comprising a promoter operably linked to a DNA segment encoding influenza virus M, a vector comprising a promoter operably linked to a DNA segment encoding influenza virus BM2, and a vector comprising a promoter operably linked to a DNA segment encoding influenza virus NS2.

28. The method of claim 24 or 26 further comprising contacting the cell with a vector comprising a promoter linked to 5' influenza virus sequences comprising 5' influenza virus noncoding sequences linked to a cDNA of interest or a fragment thereof linked to 3' influenza virus sequences comprising 3' influenza virus noncoding sequences linked to a transcription termination sequence.

29. The method of claim 24 or 26 further comprising contacting the cell with a vector comprising a RNA polymerase II promoter linked to a first ribozyme sequence linked to linked to 5' influenza virus sequences comprising 5' influenza virus noncoding sequences linked to the cDNA of interest or a fragment thereof linked to 3' influenza virus sequences comprising 3' influenza virus noncoding sequences linked to a second ribozyme sequence linked to a transcription termination sequence.

30. The method of claim 28 wherein the cDNA of interest comprises an open reading frame encodes an immunogenic polypeptide or peptide of a pathogen or a therapeutic polypeptide or peptide.

31. The method of claim 29 wherein the cDNA of interest comprises an open reading frame encodes an immunogenic polypeptide or peptide of a pathogen or a therapeutic polypeptide or peptide.

32. The method of claim 24 or 26 wherein the HA is a type A HA.

33. The method of claim 24 or 26 wherein the HA is a type B HA.

34. The method of claim 24 or 26 wherein all the vectors of a) comprise a RNA polymerase II promoter.

35. The method of claim 24 or 26 further comprising isolating the virus.

36. The composition of claim 1 wherein the influenza viral cDNA sequences in the vector having the RNA polymerase II promoter correspond to a single viral genomic segment.

37. The composition of claim 1 which, when introduced to a vertebrate cell, yields influenza virus titers substantially the same as those obtained from a vertebrate cell transfected with a composition comprising a plurality of vectors for influenza virus production comprising vectors for vRNA production which comprise a PolI promoter and a PolI terminator sequence and vectors for mRNA production for at least PA, PB1, PB2 and NP.

38. The method of claim 20, 24 or 26 wherein the influenza virus titers are substantially the same as those obtained from a vertebrate cell transfected with a plurality of vectors for influenza virus production comprising vectors for vRNA production which comprise a PolI promoter and a PolI terminator sequence and vectors for mRNA production for at least PA, PB1, PB2 and NP.

39. A vertebrate cell comprising a plurality of vectors, comprising
  a) vectors for vRNA production including a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein at least one vector comprises a RNA polymerase II promoter 5' to a first ribozyme sequence which is 5' to the viral cDNA which is 5' to a second ribozyme sequence which is 5' to the transcription termination sequence, wherein any vector for vRNA production which does not have a RNA polymerase II promoter, has a RNA polymerase I promoter; and
  b) vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, or a vector comprising a promoter operably linked to a DNA segment encoding influenza virus NP; and
  wherein the vectors are in present in the cell in an amount that yields titers of infectious influenza virus of at least $5 \times 10^3$ pfu/mL.

40. A method to prepare influenza virus, comprising contacting a vertebrate cell with a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising a promoter operably linked to an influenza virus NP cDNA linked to a transcription termination sequence, a vector for vRNA production comprising a promoter operably linked to an influenza virus NA cDNA linked to a transcription termination sequence, a vector for vRNA production comprising a promoter operably linked to an influenza virus M cDNA linked to a transcription termination sequence, and a vector for vRNA production comprising a promoter operably linked to an influenza virus NS cDNA linked to a transcription termination sequence, a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, wherein the promoter in at least one vector for vRNA production comprises a RNA polymerase II promoter 5' to a first ribozyme sequence which is 5' to the viral cDNA which is 5' to a second ribozyme sequence which is 5' to a transcription termination sequence, wherein any vector for vRNA production which does not have a RNA polymerase II promoter, has a RNA polymerase I promoter, so as to yield titers of infectious influenza virus that are substantially the same as those obtained from a vertebrate cell transfected with a plurality of vectors for influenza virus production comprising vectors for vRNA production for each of PA, PB1, PB2, HA, NP, NA, M and NS which comprise a PolI promoter and a PolI terminator sequence and vectors for mRNA production for at least PA, PB1, PB2 and NP.

41. The composition of claim 1 wherein the first and second ribozyme sequences are for different ribozymes.

42. The method of claim 24 wherein the first and second ribozyme sequences are for different ribozymes.

* * * * *

UNITED STATES PATENT AND TRADEMARK OFFICE
CERTIFICATE OF CORRECTION

PATENT NO. : 7,723,094 B2
APPLICATION NO. : 10/855975
DATED : May 25, 2010
INVENTOR(S) : Yoshihiro Kawaoka et al.

It is certified that error appears in the above-identified patent and that said Letters Patent is hereby corrected as shown below:

In column 49, line 16, in Claim 29, after "sequence" delete "linked to".

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,723,094 B2 | Page 1 of 1 |
| APPLICATION NO. | : 10/855975 | |
| DATED | : May 25, 2010 | |
| INVENTOR(S) | : Yoshihiro Kawaoka et al. | |

It is certified that error appears in the above-identified patent and that said Letters Patent is hereby corrected as shown below:

In the Specification

Column 1, Lines 16-20:
Delete the phrase:
"This invention was made with a grant from the Government of the United States of America (grant AI-47446 from the National Institute of Allergy and Infectious Diseases Public Health Service). The Government may have certain rights in the invention."

And replace with:
--This invention was made with government support under AI047446 awarded by the National Institutes of Health. The government has certain rights in the invention.--.

Signed and Sealed this
First Day of December, 2020

Andrei Iancu
*Director of the United States Patent and Trademark Office*